United States Patent
Yamamoto et al.

(10) Patent No.: US 10,161,839 B2
(45) Date of Patent: Dec. 25, 2018

(54) APPARATUS FOR MEASURING COEFFICIENT OF RESTITUTION AND HARDNESS TESTER

(71) Applicants: Yamamoto Scientific Tool Laboratory Co., Ltd., Chiba (JP); National Institute for Materials Science, Ibaraki (JP)

(72) Inventors: Takashi Yamamoto, Chiba (JP); Kensuke Miyahara, Ibaraki (JP); Tsutomu Obata, Chiba (JP); Koji Kadogawa, Chiba (JP)

(73) Assignees: YAMAMOTO SCIENTIFIC TOOL LABORATORY CO., LTD., Chiba (JP); NATIONAL INSTITUTE FOR MATERIALS SCIENCE, Ibaraki (JP)

( * ) Notice: Subject to any disclaimer, the term of this patent is extended or adjusted under 35 U.S.C. 154(b) by 100 days.

(21) Appl. No.: 15/334,786

(22) Filed: Oct. 26, 2016

(65) Prior Publication Data

US 2017/0131193 A1   May 11, 2017

(30) Foreign Application Priority Data

Nov. 5, 2015   (JP) ................................. 2015-217868
Mar. 7, 2016   (JP) ................................. 2016-043386

(51) Int. Cl.
  *G01N 3/307* (2006.01)
  *G01N 3/52* (2006.01)
  (Continued)

(52) U.S. Cl.
  CPC .............. *G01N 3/307* (2013.01); *G01N 3/52* (2013.01); *G01P 3/36* (2013.01); *G01P 3/68* (2013.01);
  (Continued)

(58) Field of Classification Search
  CPC .. G01N 3/52; G01N 2203/0083; G01N 3/307; G01N 3/48; G01P 3/36; G01V 8/20
  See application file for complete search history.

(56) References Cited

U.S. PATENT DOCUMENTS 3,896,657 A   7/1975 Brandt et al.
4,034,603 A   7/1977 Leeb et al.
(Continued)

FOREIGN PATENT DOCUMENTS

| JP | 62-124436 | 6/1987 |
|----|-----------|--------|
| JP | 7-31106   | 4/1995 |
| JP | 2011-75307 | 4/2011 |

OTHER PUBLICATIONS

"Shore hardness test—Verification of testing machines", Investigated by Japanese Industrial Standards Committee, published by Japanese Standards Association, Jul. 31, 2000 (with English translation).

(Continued)

*Primary Examiner* — Freddie Kirkland, III
(74) *Attorney, Agent, or Firm* — Wenderoth, Lind & Ponack, L.L.P.

(57) ABSTRACT

An apparatus for measuring for measuring coefficient of restitution which is capable of reducing a mass effect and performing tests in free directions, is disclosed. The apparatus for measuring coefficient of restitution includes a holder for holding a spherical indenter, an ejection mechanism configured to eject the indenter held by the holder from the holder to a specimen, a speed measuring unit configured to measure an impact speed that is a speed of the indenter before the indenter impacts against the specimen, and a rebound speed that is a speed of the indenter after the indenter is rebounded from the specimen; and an arithmetic (Continued)

unit configured to calculate a coefficient of restitution that is a ratio of the rebound speed to the impact speed.

27 Claims, 24 Drawing Sheets

(51) Int. Cl.
  *G01P 3/36* (2006.01)
  *G01V 8/20* (2006.01)
  *G01P 3/68* (2006.01)
(52) U.S. Cl.
  CPC ......... *G01V 8/20* (2013.01); *G01N 2203/001* (2013.01); *G01N 2203/0035* (2013.01); *G01N 2203/0044* (2013.01); *G01N 2203/0083* (2013.01)

(56) References Cited

U.S. PATENT DOCUMENTS

| | | | | |
|---|---|---|---|---|
| 6,354,148 | B2* | 3/2002 | Sato | G01N 3/52 |
| | | | | 73/79 |
| 6,804,988 | B2* | 10/2004 | McNamara | A63B 47/008 |
| | | | | 73/12.01 |
| 7,127,933 | B2* | 10/2006 | Correia | G01N 3/48 |
| | | | | 73/12.11 |
| 7,150,178 | B2* | 12/2006 | Bissonnette | A63B 47/008 |
| | | | | 73/12.01 |
| 8,074,496 | B2* | 12/2011 | Brandestini | G01N 3/48 |
| | | | | 713/323 |
| 2001/0010170 | A1 | 8/2001 | Sao et al. | |
| 2005/0034506 | A1 | 2/2005 | Bissonnette et al. | |
| 2006/0032288 | A1* | 2/2006 | Correia | G01N 3/48 |
| | | | | 73/12.11 |

OTHER PUBLICATIONS

M. Nakamura et al., "Impact Hardness Testing Method", Journal of Material Testing Research Association, vol. 32, No. 1, pp. 23-30, Jan. 1987 (with English translation).

S. Maki et al., "Computer Simulation of the Impact Hardness", Journal of Material Testing Research Association, vol. 42, No. 2, pp. 29-34, Apr. 1997 (with English language abstract).

M. Yamamoto et al., "Proof experiments on small and hard ball rebound hardness test using free fall", Journal of Material Testing Research Association, vol. 56, No. 4, pp. 21-26, Oct. 2011 (with partial English translation).

T. Yamamoto et al., "Evaluation of the Usefulness of Small Hard Ball Rebound Hardness Test using Hardness Standard Block", Proceedings of the 72nd Conference of the Japan Society for Heat Treatment, pp. 35-36, Dec. 2011 (with partial English translation).

S. Maki et al., "Computer Simulation of the Micro Rebound Hardness", Journal of Material Testing Research Association, vol. 58, No. 2, pp. 3-8, Apr. 2013 (with partial English translation).

T. Yamamoto et al., "Discussion on mass effect of rebound hardness through development of small ball rebound hardness testing machine", Journal of Material Testing Research Association, vol. 58, No. 2, pp. 9-14, Apr. 2013 (partial English translation).

T. Yamamoto et al., "Study of Mass Effect in New Rebound Hardness HNM Test", Proceedings of the 75th Conference of the Japan Society for Heat Treatment, pp. 29-30, Jun. 2013 (partial English translation).

T. Yamamoto et al., "Development of New Rebound Hardness— Aiming for Portable Tester Capable of Measuring Small Lightweight Test Piece—", Inspection Engineering published by Japan Industrial Publishing Co., Ltd., vol. 19, No. 1, pp. 45-53, Jan. 2014 (partial English translation).

T. Yamamoto, "Rebound tests for wide range materials by small ball rebound tester HNM", Journal of Material Testing Research Association, vol. 59, No. 3, pp. 46-50, Jul. 2014 (partial English translation).

M. Yamamoto et al., "Proof Examination on Small Rebound Hardness Carried Out With HLD/HLE Standard Blocks", XX IMEKO World Congress, Metrology for Green Growth, Sep. 9-14, 2012, Busan, Republic of Korea.

T. Yamamoto et al., "Discussion on the Mass Effect of Rebound Hardness Through the Development of the Small Ball Rebound Hardness 1 Lsting Machine", I IMEKO 22nd TC3, 15th TC5 and 3rd TC22 International Conferences, Feb. 3-5, 2014, Cape Town, Republic of South Africa.

Extended European Search Report dated Mar. 27, 2017 in European Application No. 16196207.1.

* cited by examiner

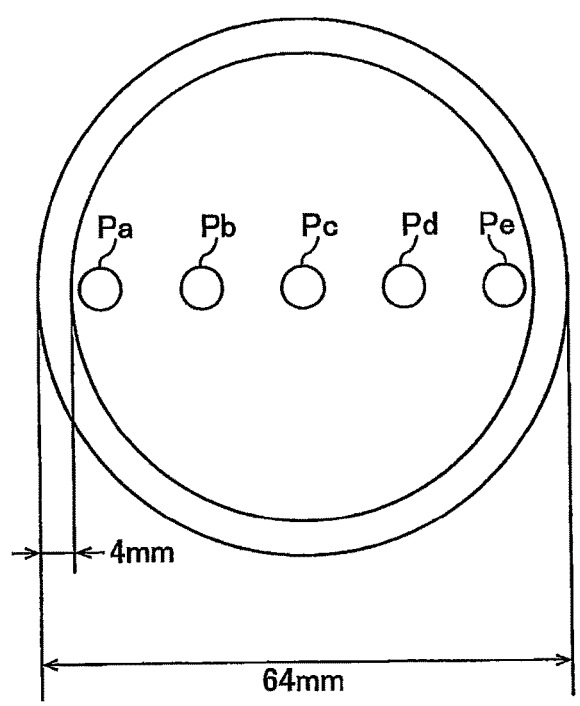

APPARATUS FOR MEASURING COEFFICIENT OF RESTITUTION AND HARDNESS TESTER

CROSS REFERENCE TO RELATED APPLICATIONS

This document claims priorities to Japanese Patent Application No. 2015-217868 filed Nov. 5, 2015 and Japanese Patent Application No. 2016-043386 filed Mar. 7, 2016, the entire contents of which are hereby incorporated by reference.

BACKGROUND

Rebound hardness tests have been used to measure the hardness of specimen, particularly metal material. In the rebound hardness test, generally, an impactor which is constructed by an indenter made of a hard material such as diamond or the like and an indenter support member to which the indenter is secured, is impacted against the surface of the specimen, and a rebound height or a rebound speed of the impactor that has been rebounded from the specimen is measured to thereby measure the hardness of the specimen. Such rebound hardness tests include the Shore hardness test and the Leeb hardness test.

The Shore hardness test, which is specified as a rebound hardness test in JIS (Japanese Industrial Standards), is a hardness testing method in which a hammer serving as the impactor freely drops from a predetermined height (drop height) onto a specimen, and the rebound height representing a maximum point reached by the hammer that has been rebounded from the specimen is measured (see JIS B 7727:2000 "Shore hardness test—Verification of testing machines"). In the Shore hardness test, the hammer is the impactor and includes an indenter and an indenter support member to which the indenter is secured. The Shore hardness is obtained by multiplying a ratio of the rebound height to the drop height of the hammer by a predetermined proportionality constant.

The Leeb hardness test is a hardness testing method in which an impact body serving as the impactor is ejected toward a specimen by a spring, and an impact speed of the impact body before impacting against the specimen and a rebound speed of the impact body when impacting against the specimen and rebounded therefrom (i.e., the speed of the impact body after impacting against the specimen) are measured (see U.S. Pat. No. 4,034,603). In the Leeb hardness test, the impact body is an impactor and includes an indenter and an indenter support member to which the indenter is secured. In the Leeb hardness test, a ratio of the rebound speed of the impact body to the impact speed of the impact body serving as the impactor is measured as a coefficient of restitution. The Leeb hardness is obtained by multiplying the coefficient of restitution by a predetermined proportionality constant.

The rebound hardness tests, which are typified by the Shore hardness test and the Leeb hardness test, are advantageous in that testing of the hardness can be simply and quickly performed, compared with indentation hardness tests such as the Rockwell hardness test and the Vickers hardness test. Furthermore, testers for use in the rebound hardness tests are advantageous in that they have a simple structure and excellent portability, compared with testers for use in the indentation hardness tests.

However, a mass of the hammer for use in the Shore hardness test, and a mass of the impact body for use in the Leeb hardness test are comparatively large. For example, the mass of the hammer of a D-type Shore hardness tester is 36.2 g and the mass of the impact body of the Leeb hardness tester is 5.45 g. When the hardness of a small and light specimen is measured using such hammer or impact body, only a hardness value lower than the true hardness value of this specimen may be obtained.

The reason of this is that the kinetic energy of the impactor (i.e., the hammer or the impact body including the indenter and the indenter support member) which impacts against the small and light specimen is consumed by not only plastic deformation and elastic deformation of the specimen, but also vibrations or the like, of the specimen, resulting in the measurement of a rebound height or a rebound speed which is smaller than the rebound height or the rebound speed to be measured normally. This phenomenon, i.e., the phenomenon that a smaller rebound height or rebound speed than the rebound height or rebound speed to be measured normally, is measured as a result of the consumption of the kinetic energy of the impactor by vibration or the like, of the specimen, will be referred to as "mass effect" in the present specification.

If the mass effect occurs when the hardness of the specimen is measured, a correct hardness of the specimen cannot be obtained. Therefore, when the hardness of a specimen having a mass of 4 kg or less is to be measured by the Shore hardness test, it is necessary to perform the test while the specimen is firmly secured to a dedicated steel anvil having a sufficiently large mass. In the Leeb hardness test, a dedicated anvil is not prepared. Thus, when the hardness of the small and light specimen is to be measured by the Leeb hardness test, it is necessary for the user to prepare an appropriate support having a sufficiently large mass, and firmly secure the specimen to the support using a dedicated paste. Specifically, there have been restrictions on the size and mass of the specimen to be tested when its hardness is to be correctly measured by conventional rebound hardness testers.

In the Shore hardness test, since it is necessary to measure the rebound height after the hammer has dropped freely from a predetermined drop height to impact with the specimen, the testing direction of the Shore hardness test is limited to a vertical direction. On the other hand, in the Leeb hardness test, the impact body is ejected toward the specimen by the spring, and the coefficient of restitution which represents the ratio of the rebound speed of the impact body to the impact speed thereof before the impact body impacts against the specimen is measured. Accordingly, the Leeb hardness test is capable of measuring, in a free direction, the coefficient of restitution and the hardness based on the coefficient of restitution.

According to the hardness testing method, such as the Leeb hardness test, in which an impactor is ejected by the spring to measure the coefficient of restitution of the specimen and this coefficient of restitution is used as an index for evaluating the hardness of the specimen, the hardness test can be performed while the tester is oriented in a free direction. However, when the specimen to measure the hardness is small and light, the mass effect occurs even in the Leeb hardness test. Therefore, there have been demands for an apparatus for measuring coefficient of restitution and a hardness tester which are capable of reducing the mass effect and performing tests in free directions.

SUMMARY OF THE INVENTION

According to embodiments, there are provided an apparatus for measuring coefficient of restitution and a hardness tester which are capable of reducing the mass effect and performing tests in free directions.

Embodiments, which will be described below, relate to an apparatus for measuring coefficient of restitution that is used as an index for evaluating hardness of a specimen. The below-described embodiments further relate to a hardness tester for measuring hardness of a specimen.

In an embodiment, there is provided an apparatus for measuring coefficient of restitution, including: a holder for holding a spherical indenter; an ejection mechanism configured to eject the indenter held by the holder from the holder to a specimen; a speed measuring unit configured to measure an impact speed that is a speed of the indenter before the indenter impacts against the specimen, and a rebound speed that is a speed of the indenter after the indenter is rebounded from the specimen; and an arithmetic unit configured to calculate a coefficient of restitution that is a ratio of the rebound speed to the impact speed.

In an embodiment, the holder has a tubular shape, a front end of the holder is constituted of a plurality of divided portions by forming slits extending parallel to an axis of the holder, and the holder holds a circumferential surface of the indenter at the divided portions.

In an embodiment, the ejection mechanism includes an inner cylinder with a through hole formed therein, an outer cylinder having an inner circumferential surface slidably supported by an outer circumferential surface of the inner cylinder, an indenter pushing member movable in the through hole, and a biasing spring which is disposed between the outer cylinder and the indenter pushing member, and is compressed by movement of the outer cylinder to apply a biasing force to the indenter pushing member, and the outer cylinder has an ejection lever which can engage with a groove formed on an outer surface of the indenter pushing member.

In an embodiment, the indenter pushing member is a striker which collides with the indenter held by the holder.

In an embodiment, the indenter pushing member is a piston rod which applies an air pressure to the indenter held by the holder.

In an embodiment, the speed measuring unit includes a speed measuring body having an indenter channel which is connected to the through hole, and a first passage sensor and a second passage sensor which are arrayed along the indenter channel.

In an embodiment, the first passage sensor and the second passage sensor are optical sensors.

In an embodiment, the speed measuring unit further includes a third passage sensor, the first passage sensor, the second passage sensor, and the third passage sensor are arrayed along the indenter channel, and the arithmetic unit calculates an acceleration of the indenter from a speed of the indenter passing between the first passage sensor and the second passage sensor, and a speed of the indenter passing between the second passage sensor and the third passage sensor, and further calculates an impact speed at the instant at which the indenter impacts against the specimen, and a rebound speed at the instant at which the indenter is rebounded from the specimen.

In an embodiment, the first passage sensor, the second passage sensor, and the third passage sensor are optical sensors.

In an embodiment, the speed measuring unit includes a speed measuring body having an indenter channel which is connected to the through hole, and a first passage sensor and a second passage sensor which are arrayed along the indenter channel, the first passage sensor is an optical sensor having a first light emitter and a first light receiver, the second passage sensor is an optical sensor having a second light emitter and a second light receiver, the first light emitter emits light through a first optical fiber into the indenter channel, and the first light receiver receives the light emitted into the indenter channel through a second optical fiber, the second light emitter emits light through a third optical fiber into the indenter channel, and the second light receiver receives the light emitted into the indenter channel through a fourth optical fiber.

In an embodiment, the speed measuring unit includes a speed measuring body having an indenter channel which is connected to the through hole, and a first passage sensor which is disposed in the indenter channel, the arithmetic unit detects a detection starting point of time of the indenter at the first passage sensor and a detection ending point of time of the indenter at the first passage sensor, and the arithmetic unit calculates the impact speed and the rebound speed by dividing a diameter of the indenter by a time between the detection starting point of time and the detection ending point of time.

In an embodiment, the speed measuring unit includes a speed measuring body having an indenter channel which is connected to the through hole, and the speed measuring body has a shutter mechanism which opens an opening of the indenter channel when the speed measuring unit contacts the specimen, and closes the opening of the indenter channel when the speed measuring unit is separated from the specimen.

In an embodiment, the shutter mechanism includes a door disposed at the opening of the indenter channel, an opening/closing rod whose front end projects from the speed measuring body, and a link mechanism for converting movement of the opening/closing rod into opening/closing movement of the door.

In an embodiment, the speed measuring unit includes a speed measuring body having an indenter channel which is connected to the through hole, a lid is fixed to a front end of the speed measuring body, the lid having a lid through hole which is connected to the indenter channel, and the lid through hole has a diameter which is greater than 0.2 times a diameter of the indenter, and is smaller than the diameter of the indenter.

In an embodiment, a wall surface of the lid through hole is forming in a curved surface, and a radius of curvature of the wall surface is greater than a radius of curvature of the indenter.

In an embodiment, a vent hole extending from a side surface of the speed measuring body to the indenter channel, is formed in the speed measuring body.

In an embodiment, the indenter channel has a diameter which is 1.4 times the diameter d of the indenter or greater.

In an embodiment, the speed measuring unit includes a speed measuring body having an indenter channel which is connected to the through hole, a coupling mechanism for coupling the holder to the outer cylinder is further provided, and when the outer cylinder moves toward the speed measuring unit, the holder moves in the forward direction in the indenter channel to hold the indenter which exists in the indenter channel.

In an embodiment, the indenter is made of ceramics.

In an embodiment, the indenter is a bearing ball made of alumina.

In an embodiment, a diameter of the indenter is in a range from 0.5 mm to 5 mm.

In an embodiment, there is provided a hardness tester, comprising: a holder for holding a spherical indenter; an ejection mechanism configured to eject the indenter held by the holder from the holder to a specimen; a speed measuring unit configured to measure an impact speed that is a speed of the indenter before the indenter impacts against the specimen, and a rebound speed that is a speed of the indenter after the indenter is rebounded from the specimen; and an arithmetic unit configured to decide hardness of the specimen based on a ratio of the rebound speed to the impact speed.

According to the above-described embodiments, an impactor (object) that impacts against the specimen for measuring the coefficient of restitution is only the spherical indenter. More specifically, the impactor that impacts against the specimen does not include an indenter support to which the indenter would be fixed, unlike the hammer for use in the Shore hardness test and the impact body for use in the Leeb hardness test, for example. As a result, since the mass of the impactor (object) that impacts against with the specimen is greatly reduced, the mass effect occurring when the coefficient of restitution is to be measured is greatly reduced, thereby enabling the coefficient of restitution of the specimen to be correctly measured. Further, the spherical indenter is held in the holder, and ejected from the holder toward the specimen by the ejection mechanism. Therefore, since there is no limitation on the direction in which the indenter is ejected, the test can be performed in a free direction.

Further, according to the above-described embodiments, an impactor (object) that impacts against the specimen for measuring the hardness is only the spherical indenter. As a result, since the mass of the impactor (object) that impacts against with the specimen is greatly reduced, the mass effect occurring when the hardness is to be measured is greatly reduced, thereby enabling the hardness of the specimen to be correctly measured.

BRIEF DESCRIPTION OF THE DRAWINGS

FIG. 17 is a plan view of a standard block used in experiment;

DESCRIPTION OF EMBODIMENTS

Embodiments will be described below with reference to the accompanying drawings.

Figure 1:
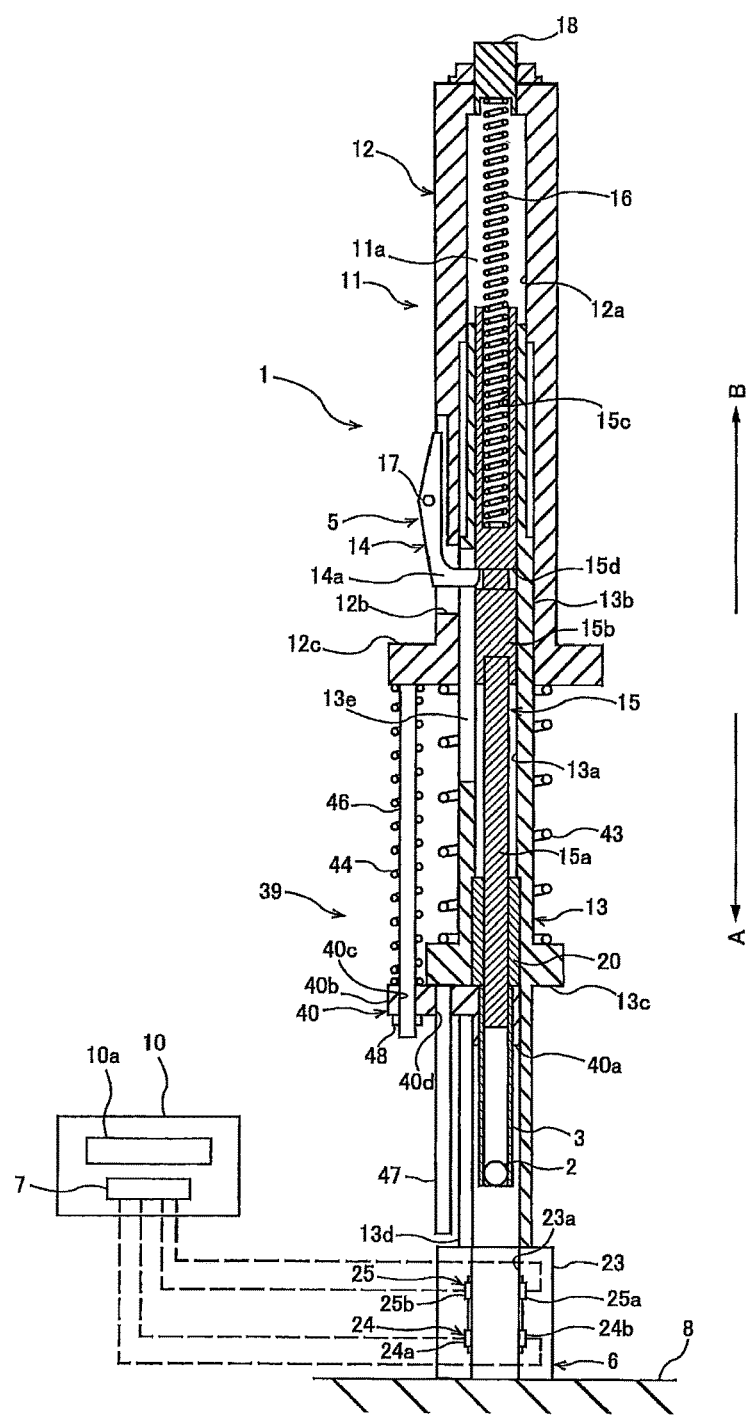
FIG. 1 is a schematic cross-sectional view showing an apparatus for measuring coefficient of restitution according to an embodiment.

FIG. 1 is a schematic cross-sectional view showing an apparatus 1 for measuring coefficient of restitution according to an embodiment. For convenience in description, in the present specification, the direction indicated by arrow A shown in FIG. 1 is defined as a forward direction, and the direction indicated by arrow B is identified as a backward direction.

The apparatus 1 for measuring coefficient of restitution shown in FIG. 1 has a holder 3 for holding a spherical indenter 2, an ejection mechanism 5 for ejecting the indenter 2 held by the holder 3 from this holder 3 toward a specimen 8, a speed measuring unit 6 for measuring an impact speed which represents the speed of the indenter 2 before the indenter 2 impacts against the specimen 8 and a rebound speed of the indenter 2 after the indenter 2 impacts against the specimen 8 and rebounds therefrom, and an arithmetic unit 7 for calculating a coefficient of restitution which represents the ratio of the rebound speed to the impact speed. The arithmetic unit 7 is disposed in a display unit 10 having a display 10a for displaying the coefficient of restitution calculated by the arithmetic unit 7.

Figure 2A:
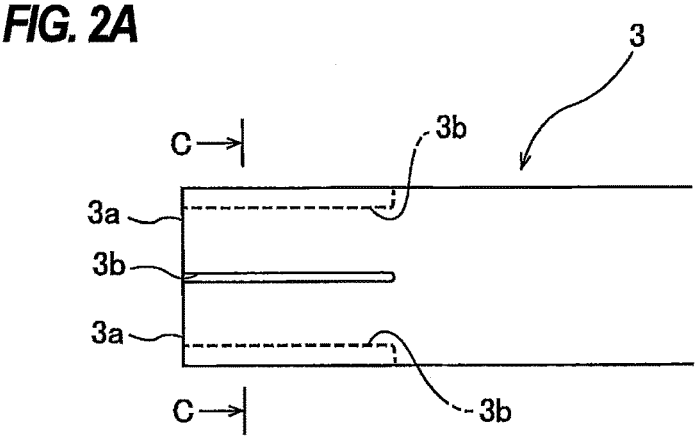
FIG. 2A is an enlarged side view showing a front end of a holder.
Figure 2B:
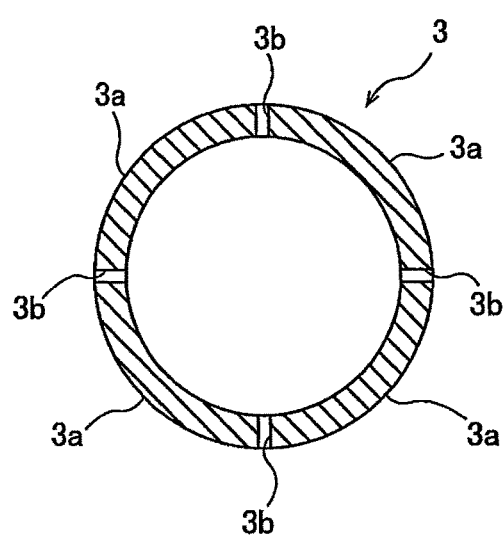
FIG. 2B is a cross sectional view taken along line C-C in FIG. 2A.

The holder 3 shown in FIG. 1 has a hollow cylindrical shape. As shown in FIGS. 2A and 2B, the front end of the holder 3 is constituted of a plurality of divided portions 3a by forming slits 3b extending parallel to the axis of the holder 3. In the illustrated example, the front end of the holder 3 is constituted of four divided portions 4b by four slits 3b. The front end of the holder 3 may be constituted of three or less divided portions 3a or five or more divided portions 3a. The diameter of the inner circumferential surface of the holder 3 is slightly smaller than the diameter of the spherical indenter 2, so that when the front end of the holder 3 is pressed against the indenter 2, the divided portions 3a are slightly spread in an outer circumferential direction of the holder 3 and an outer circumferential surface of the indenter 2 is held by the plurality of divided portions 3a.

The shape of holder 3 is not limited to the hollow cylindrical shape, but may be of a tubular shape. For example, the holder 3 may have a polygonal tubular shape such as a square tubular shape, a pentagonal tubular shape, or the like. Even though the holder 3 has a polygonal tubular shape, the slits extending parallel to the axis of the holder 3 are formed in the front end of the holder 3 and the front end of the holder 3 is constituted of a plurality of divided portions. When the front end of the holder 3 having a polygonal tubular shape is pressed against the indenter 2, the divided portions are slightly spread outwardly of the holder 3, and the inner circumferential surface of the indenter 2 is held by the divided portions.

As shown in FIG. 1, the ejection mechanism 5 according to the present embodiment has an inner cylinder 13 with a through hole 13a formed therein, an outer cylinder 12 having an inner circumferential surface 12a slidably supported by an outer circumferential surface 13b of the inner cylinder 13, a striker 15 movable in the through hole 13a, and a biasing spring 16 which is disposed between the outer cylinder 12 and the striker 15, and is compressed by movement of the outer cylinder 12 to thereby apply a biasing force to the striker 15. Furthermore, the ejection mechanism 5 shown in FIG. 1 has a stopper 20 for restricting movement of the striker 15 in the through hole 13a. Although not shown, the stopper 20 may be omitted. For example, by fixing a front end of the biasing spring 16 to the striker 15, forward movement of the striker 15 in the through hole 13a can be restricted. A wall surface of the through hole 13a is the inner circumferential surface of the inner cylinder 13. As will be described later, the striker 15 constitutes an indenter pushing member that collides with the indenter 2, which is held by the holder 3, with use of the spring force from the biasing spring 16.

The striker 15 according to the present embodiment has a rod shape. More specifically, this striker 15 includes a cylindrical striker body 15a and a cylindrical body support 15b having a greater diameter than the diameter of the striker body 15a. The striker body 15a has its back end embedded in the front end of the body support 15b, so that the striker body 15a is fixed to the body support 15b. The central axis of the striker body 15a is in alignment with the central axis of the body support 15b. The striker body 15a may be integrally formed with the body support 15b. For example, a cylindrical member may be ground to form the strike body 15a on the striker 15.

A front end of the biasing spring 16 is inserted into a guide hole 15c which is formed in the body support 15b. The guide hole 15c extends from the back end toward front end of the body support 15b, and the central axis of the guide hole 15c is in alignment with the central axis of the body support 15b. To the back end of the outer cylinder 12, a plug 18 that closes an opening of the outer cylinder 12 is fixed, and a back end of the biasing spring 16 is supported by the plug 18. The plug 18 according to the present embodiment has a cylindrical shape, and a screw thread is formed on an outer circumferential surface of the plug 18. An opening formed on the back end of the outer cylinder 12 is constructed as a threaded hole into which the screw thread formed on the outer circumferential surface of the plug 18 is screwed. The screw thread formed on the plug 18 engages with the threaded hole, thereby securing the plug 18 to the outer cylinder 12. By rotating the plug 18, the plug 18 can be moved forwards or backwards relative to the outer cylinder 12. As a result, the biasing force applied to the striker 15 from the biasing spring 16 can be easily changed, because a length of the biasing spring 16 can be easily changed.

With these configurations, the biasing spring 16 is disposed between the outer cylinder 12 and the striker 15. The biasing spring 16 is compressed by movement of the outer cylinder 12, thereby allowing the biasing force to be applied to the striker 15. The compressing operation of the biasing spring 16 will be described later. As shown in FIG. 1, when the biasing spring 16 is compressed, the biasing spring 16 applies the biasing force for moving the striker 15 in the forward direction of the ejection mechanism 5, to the striker 15. This position of the striker 15 is an ejection position of the striker 15.

An annular groove 15d extending along a circumferential direction of the striker 15 is formed on the outer surface of the body support 15b. The groove 15d may be formed on a part of the outer surface of the body support 15b. An ejection lever 15 is fixed to the outer surface of the outer cylinder 11, the ejection lever 15 having a hook 14a that can engage with the groove 15d when the striker 15 is in the ejected position shown in FIG. 1. The ejection lever 14 has a through hole, and a rotational shaft 17 which is secured to a bracket (not shown) extending radially outwardly from the outer surface of the outer cylinder 11, is inserted into this through hole. Therefore, the ejection lever 14 is mounted to the outer cylinder 12 so as to be able to pivot around the rotational shaft 17. As shown in FIG. 1, the outer cylinder 12 has a through hole 12b which penetrates through a side wall of the outer cylinder 12, and the inner cylinder 13 has a first elongated hole 13e which penetrates through a side wall of the inner cylinder 13 and extends along a longitudinal direction of the inner cylinder 13. The hook 14a of the ejection lever 14 passes through the through hole 12*b* of the outer cylinder 12 and the first elongated hole 13*e* of the inner cylinder 13 to engage with the groove 15*d* of the striker 15.

Figure 3:
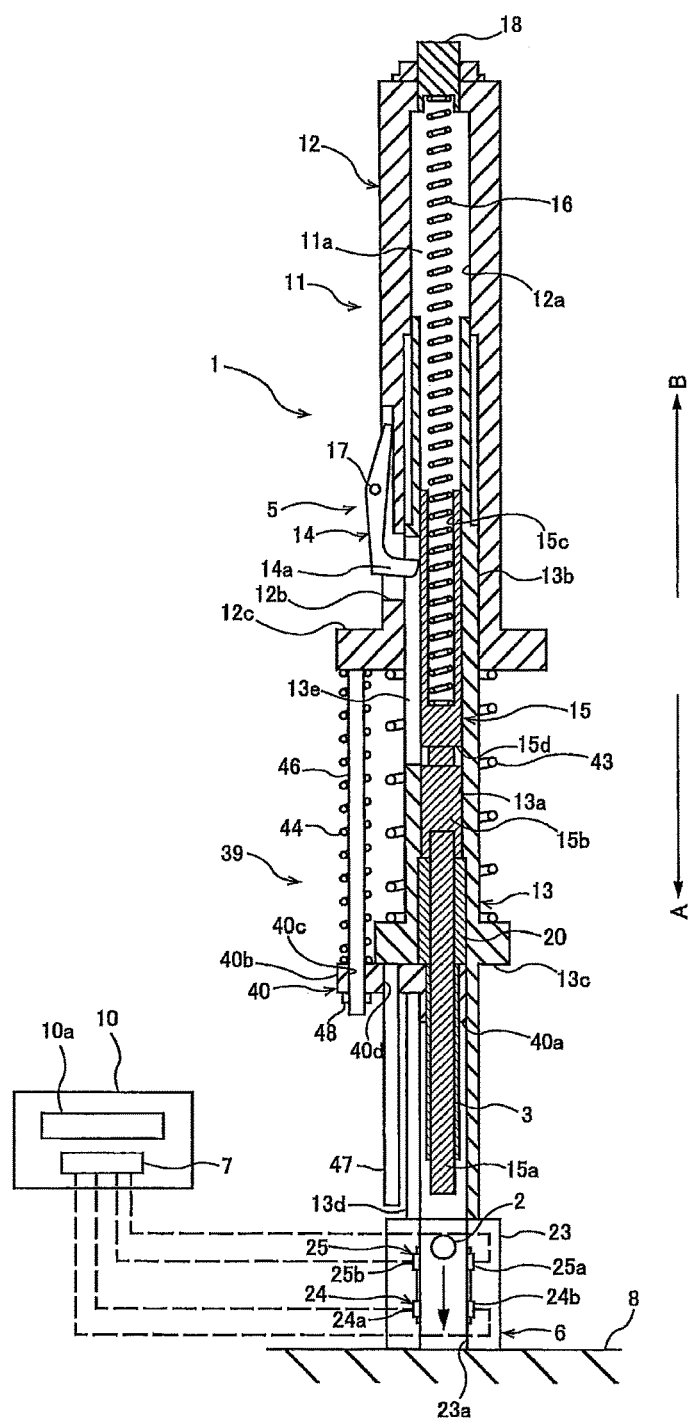
FIG. 3 is a schematic cross-sectional view showing a state in which a striker is pushed out in a forward direction with use of a spring force of a biasing spring when a hook of an ejection lever disengages from a groove of the striker.

FIG. 3 is a schematic cross-sectional view showing a state in which the striker 15 is pushed out in the forward direction of the ejection mechanism 5 with use of the spring force of the biasing spring 16 when the hook 14*a* of the ejection lever 14 disengages from the groove 15*d* of the striker 15. As shown in FIG. 3, the striker 15 that has been pushed out in the forward direction of the ejection mechanism 5, collides with the stopper 20, which has a hollow cylindrical shape and is fixed to the inner circumferential surface of the inner cylinder 13, and as a result, the forward movement of the striker 15 is restricted. More specifically, the front end of the body support 15*b* of the striker 15 collides with the back end of the stopper 20, and as a result, the forward movement of the striker 15 is restricted. During the striker 15 moves from the ejection position shown in FIG. 1 to a collision position shown in FIG. 3 where it collides with the stopper 20, the front end of the striker body 15*a* collides with indenter 2 held by the front end of the holder 3, thereby ejecting only the indenter 2 from the holder 3 toward the specimen 8. As shown in FIG. 3, when the striker 15 has been ejected in the forward direction of the ejection mechanism 5, the hook 14*a* of the ejection lever 14 passes through the through hole 12*b* of the outer cylinder 12 and the first elongated hole 13*e* of the inner cylinder 13, and is in contact with the outer surface of the striker 15.

As described above, the length of the biasing spring 16 can be adjusted by moving the plug 18 supporting the back end of the biasing spring 16 forwards or backwards relative to the outer cylinder 12. Therefore, the impact speed of the indenter 2 ejected by collision with the striker 15 can be adjusted, because the biasing force applied to the striker 15 from the biasing spring 16 can be adjusted. When the coefficients of restitution of different specimens are to be compared, it is preferred that the material of the indenter 2 and the impact speed of the indenter 2 are constant. The apparatus 1 for measuring coefficient of restitution according to the present embodiment can easily adjust the impact speed of the indenter 2.

Although the striker 15 according to the above described embodiment has the rod-shape, the shape of the striker 15 is not limited to the rod shape. The shape of the striker 15 is arbitrary if it can collides with the indenter 2 held by the holder 3 to thereby eject the indenter 2 from the holder 3 toward the specimen 8.

The speed measuring unit 6 for measuring the impact speed which represents the speed of the indenter 2 before the indenter 2 ejected by the striker 15 impacts against the specimen 8, and the rebound speed of the indenter 2 after the indenter 2 impacts against the specimen 8 and rebounds therefrom, is fixed to the front end of the ejection mechanism 5, or more specifically, to the front end of the inner cylinder 13. The speed measuring unit 6 according to the present embodiment has a speed measuring body 23 which is mounted on the front end of the inner cylinder 13 and has an indenter channel 23*a* through which the indenter 2 passes, and a first passage sensor 24 and a second passage sensor 25 which are arrayed along the indenter channel 23*a*. The indenter channel 23*a* is connected to the through hole 13*a* of the inner cylinder 13. The first passage sensor 24 and the second passage sensor 25 are arrayed along the indenter channel 23*a*, and the first passage sensor 24 is positioned forwardly of the second passage sensor 25 in the speed measuring body 23. The "passage sensor" collectively refers to sensors capable of detecting the passage of an object. The passage sensor includes an optical sensor or a magnetic sensor, for example.

The first passage sensor 24 according to the present embodiment is an optical sensor having a first light emitter 24*a* for emitting light into the indenter channel 23*a* and a first light receiver 24*b* for receiving the light emitted from the first light emitter 24*a*. The second passage sensor 25 according to the present embodiment is an optical sensor having a second light emitter 25*a* for emitting light into the indenter channel 23*a* and a second light receiver 25*b* for receiving the light emitted from the second light emitter 25*a*. The embodiment in which the first passage sensor 24 and the second passage sensor 25 are the optical sensors will be described below.

In the present embodiment, light-emitting diodes (LEDs) are used as the first light emitter 24*a* and the second light emitter 25*a*, and photodiodes are used as the first light receiver 24*b* and the second light receiver 25*b*. Light from the first light emitter 24*a* is emitted into the indenter channel 23*a* through a light projection slit (not shown) disposed in a wall surface of the indenter channel 23*a*, and the first light receiver 24*b* receives light that has passed through a light receiving slit (not shown) disposed in a wall surface of the indenter channel 23*a*. Similarly, Light from the second light emitter 25*a* is emitted into the indenter channel 23*a* through a light emission slit (not shown) disposed in a wall surface of the indenter channel 23*a*, and the second light receiver 25*b* receives light that has passed through a light receiving slit (not shown) disposed in a wall surface of the indenter channel 23*a*. In the present embodiment, the first light emitter 24*a* and the first light receiver 24*b* of the first optical sensor 24 are disposed at a position which is spaced from the front end of the speed measuring body 23 by 10 mm, and the second light emitter 25*a* and the second light receiver 25*b* of the second optical sensor 25 are disposed at a position which is spaced from the front end of the speed measuring body 23 by 20 mm.

The first light receiver 24*b* detects that the light emitted from the first light emitter 24*a* is blocked by the passage of the indenter 2, whereby the first optical sensor 24 detects that the indenter 2 has passed the first optical sensor 24. Similarly, the second light receiver 25*b* detects that the light emitted from the second light emitter 25*a* is blocked by the passage of the indenter 2, whereby the second optical sensor 25 detects that the indenter 2 has passed the second optical sensor 25. The arithmetic unit 7 measures a passage time taken after the indenter 2 has passed the first optical sensor 24 until the indenter 2 passes the second optical sensor 25. The distance between the first optical sensor 24 and the second optical sensor 25 (10 mm in the present embodiment) is determined in advance. Therefore, the arithmetic unit 7 can calculate the impact speed of the indenter 2 from the passage time taken after the indenter 2 has passed the second optical sensor 25 until the indenter 2 passes the first optical sensor 24, and the distance between the first optical sensor 24 and the second optical sensor 25. Similarly, the arithmetic unit 7 can calculate the rebound speed of the indenter 2 from the passage time taken after the indenter 2 has passed the first optical sensor 24 until the indenter 2 passes the second optical sensor 25, and the distance between the first optical sensor 24 and the second optical sensor 25.

Figure 4:
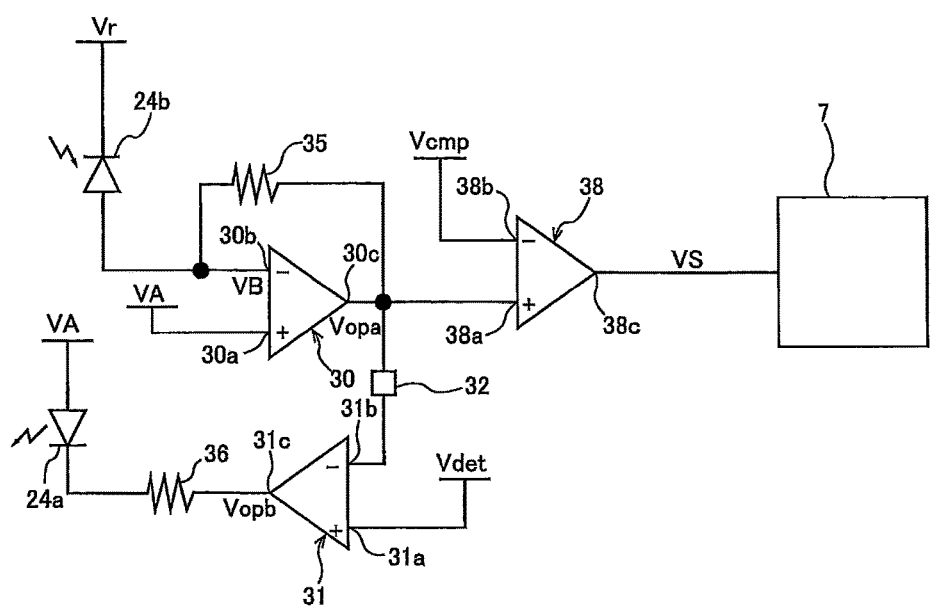
FIG. 4 is a schematic view showing an arrangement of an electric circuit of a first optical sensor.

FIG. 4 is a schematic diagram showing an arrangement of an electric circuit of the first optical sensor 24. The arrangement of the electric circuit of the first optical sensor 24 will be described below with reference to FIG. 4. An arrangement of an electric circuit of the second optical sensor 25 is identical to the arrangement of the electric circuit of the first optical sensor 24, and its repetitive explanation will be omitted.

As shown in FIG. 4, a reverse bias voltage Vr is applied to the first light receiver 24*b* which is a photodiode. The first light receiver 24*b* receives the light from the first light emitter 24*a* which is an LED, thereby generating an electric current. The electric current generated from the first light receiver 24*b* is input to a negative input terminal 30*b* of a first operational amplifier 30. A voltage VA is input to a positive input terminal 30*a* of the first operational amplifier 30. From an output terminal 30*c* of the first operational amplifier 30, a voltage Vopa, which is converted from the electric current generated from the first light receiver 24*b* by a conversion resistor 35 using the voltage VA as a reference, is output (current-to-voltage conversion).

The voltage Vopa output from the first operational amplifier 30 is input to a negative input terminal 31*b* of a second operational amplifier 31 through a delay circuit 32. A predetermined base voltage Vdet is input to a positive input terminal 31*a* of the second operational amplifier 31. The second operational amplifier 31 outputs, from a output terminal 31*c* of the second operational amplifier 31, a voltage Vopb which is a difference between the voltage Vopa input to the negative input terminal 31*b* and the base voltage Vdet input to the positive input terminal 31*a*. The voltage Vopb output from the output terminal 31*c* of the second operational amplifier 31 is converted by a conversion resistor 36 into an electric current, this electric current being applied to the first light emitter 24*a*.

As shown in FIG. 4, the voltage Vopa output from the output terminal of the first operational amplifier 30 is input to a positive input terminal 38*a* of a comparator 38. A voltage Vcmp, which is a preset threshold value, is input to a negative input terminal 38*b* of the comparator 38. The comparator 38 compares the voltage Vopa input to the positive input terminal 38*a* and the voltage Vcmp input to the negative input terminal 38*b* with each other. When the voltage Vopa is larger than the voltage Vcmp, the comparator 38 output a signal VS from its output terminal 38*c*. The signal VS is input to the arithmetic unit 7.

According to the circuit arrangement shown in FIG. 4, when the light from the first light emitter 24*a* is not blocked due to the passage of the indenter 2, the amount of light emitted from the first light emitter 24*a* can automatically be adjusted so that the voltage Vopa output from the first operational amplifier 30 converges on the preset base voltage Vdet at all times. Specifically, the electric circuit shown in FIG. 4 includes a feedback circuit for automatically changing the amount of light emitted from the first light emitter 24*a* which is the photodiode, depending on the output electric current from the first light receiver 24*b* so that the output electric current from the first light receiver 24*b* which is the photodiode becomes constant.

When the light from the first light emitter 24*a* is not blocked due to the passage of the indenter 2, it is preferred that the first light receiver 24*b*, which is the photodiode and receives the light emitted from the first light emitter 24*a* which is the LED, outputs a constant electric current at all times. However, the amount of light emitted from an LED differs depending on the environment (e.g., temperature and humidity) in which the LED is placed. Similarly, the electric current output from a photodiode differs depending on the environment (e.g., temperature and humidity) in which the photodiode is placed. Furthermore, since there are individual differences between LEDs, the amounts of light emitted from the LEDs are different from each other when the same electric current flows through the different LEDs that are of the same structure. Similarly, since there are individual differences between photodiodes, the currents output from the photodiodes are different from each other when the different photodiodes, which are of the same structure, receive the same amount of light.

Therefore, in a case where the electric circuit shown in FIG. 4 is not used, the voltage Vopa output from the operational amplifier 30 varies depending on the environment in which the apparatus 1 for measuring coefficient of restitution is placed, and thus there is the possibility that a correct coefficient of restitution cannot be measured. In order to measure the correct coefficient of restitution, it is necessary to adjust, in every measurement, the amount of light emitted from the first light emitter 24*a* and/or the output electric current from the first light receiver 24*b*. Similarly, in a case where the electric circuit shown in FIG. 4 is not used, the voltages Vopa output from the operational amplifiers 30 of different apparatus 1 for measuring coefficient of restitution are different in the respective apparatus 1 for measuring coefficient of restitution, and thus there is the possibility that a correct coefficient of restitution cannot be measured. In order to measure the correct coefficient of restitution, it is necessary to adjust, in each apparatus 1 for measuring coefficient of restitution, the amount of light emitted from the first light emitter 24*a* and/or the output electric current from the first light receiver 24*b*.

In a case where the electric circuit shown in FIG. 4 is used, the amount of light emitted from the first light emitter 24*a* can automatically be adjusted so that the voltage Vopa output from the first operational amplifier 30 converges on the preset base voltage Vdet at all times. Accordingly, it is not necessary to adjust, in every measurement, the amount of light emitted from the first light emitter 24*a* and/or the output electric current from the first light receiver 24*b*. Similarly, it is not necessary to adjust, in each apparatus 1 for measuring coefficient of restitution, the amount of light emitted from the first light emitter 24*a* and/or the output electric current from the first light receiver 24*b*. Inasmuch as the arrangement of the electric circuit of the second optical sensor 25 is identical to the arrangement of the electric circuit of the first optical sensor 24, the identical advantages are available for the optical sensor 25.

Figure 5:
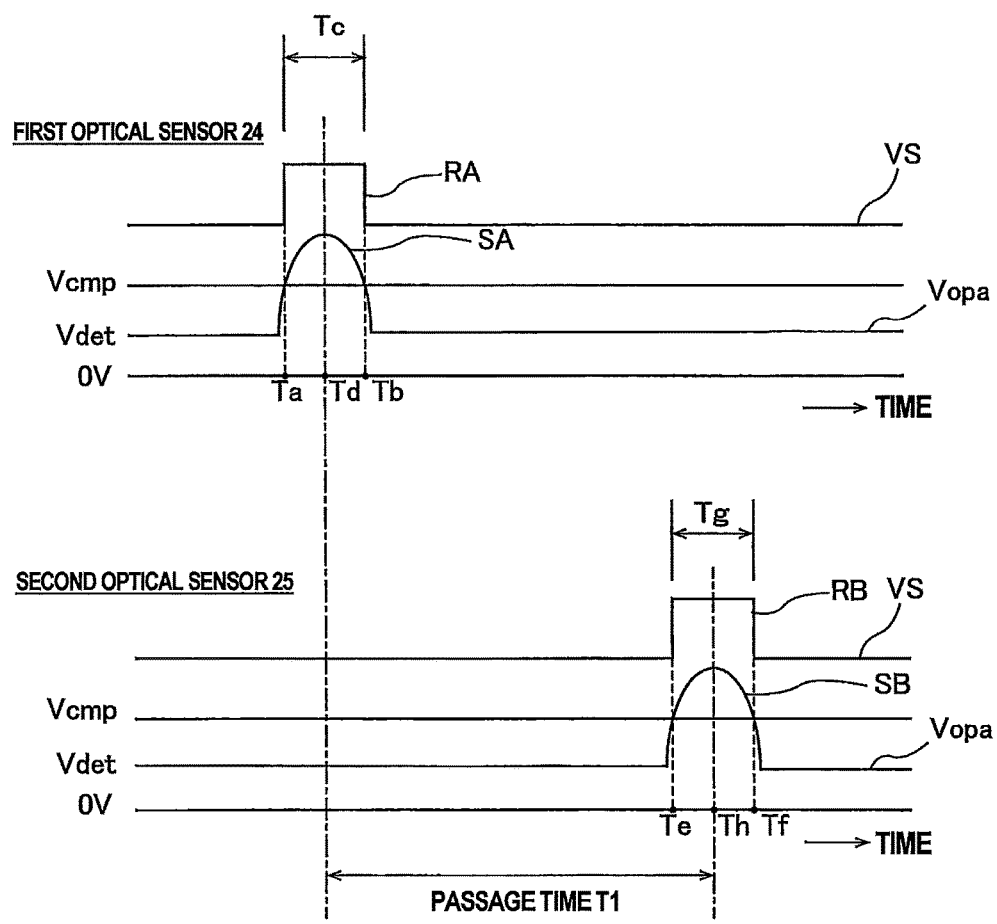
FIG. 5 is a schematic diagram illustrating a method of measuring a passage time taken after an indenter has passed the first optical sensor until the indenter passes the second optical sensor.

FIG. 5 is a schematic diagram illustrating a method of measuring a passage time T1 taken after the indenter 2 has passed the first optical sensor 24 until the indenter 2 passes the second optical sensor 25. In other words, FIG. 5 is a schematic diagram illustrating a method of measuring the rebound speed of the indenter 2 which impacts against specimen 8 and rebounds therefrom. FIG. 5 shows in its upper area a graph representing the output voltage Vopa from the first operational amplifier 30 and the signal VS output from the comparator 38, which vary over time, of the first optical sensor 24. FIG. 5 shows in its lower area a graph representing the output voltage Vopa from the first operational amplifier 30 and the signal VS output from the comparator 38, which vary over time, of the second optical sensor 25.

The indenter 2 which impacts against the specimen 8 and rebounds therefrom moves to the position where the first optical sensor 24 is disposed. When the indenter 2 blocks the light emitted from the first light emitter 24*a* of the first optical sensor 24, and thereby the amount of light received by the first light receiver 24*b* is reduced, the output voltage Vopa from the first operational amplifier 30 increases. As the indenter 2 passes the first optical sensor 24, the blocked amount of light emitted from the first light receiver 24*b* gradually decreases and thereafter gradually increases. Therefore, because the amount of light received by the first light receiver 24b gradually decreases and thereafter gradually increases, the output voltage Vopa from the first operational amplifier 30 is plotted as a wave SA having a convex waveform shown in the upper area of FIG. 5. As described above, the output voltage Vopa from the first operational amplifier 30 is input to the comparator 38 (see FIG. 4) and compared with the voltage Vcmp serving as the threshold value. When the output voltage Vopa from the first operational amplifier 30 is larger than the voltage Vcmp, the comparator 38 outputs the signal VS. When the output voltage Vopa from the first operational amplifier 30 is smaller than the voltage Vcmp, the comparator 38 stops outputting the signal VS. As a result, a rectangular wave RA converted from the wave SA having the convex waveform by the comparator 38 is input to the arithmetic unit 7.

The arithmetic unit 7 detects a point of time Ta when the signal VS is output from the comparator 38 and a point of time Tb when the outputting of the signal VS is stopped. Specifically, the point of time Ta is a detection starting point of time when the arithmetic unit 7 starts detecting of the passage of indenter 2 at the first optical sensor 24, and the point of time Tb is a detection ending point of time when the arithmetic unit 7 ends detecting of the passage of indenter 2 at the first optical sensor 24. The arithmetic unit 7 calculates a time Td by halving a time Tc taken after the point of time Ta has been detected until the point of time Tb is detected. The time Tc corresponds to a time during which the arithmetic unit 7 is detecting the passage of indenter 2 at the first optical sensor 24.

The indenter 2 further moves on to the position where the second optical sensor 25 is disposed. When the indenter 2 blocks the light emitted from the second light emitter 25a of the second optical sensor 25, reducing the amount of light detected by the second light receiver 25b, the output voltage Vopa from the first operational amplifier 30 increases. As the indenter 2 passes the second optical sensor 25, the blocked amount of light emitted from the second light receiver 25b gradually decreases and thereafter gradually increases. Therefore, because the amount of light detected by the second light receiver 25b gradually decreases and thereafter gradually increases, the output voltage Vopa from the first operational amplifier 30 is plotted as a wave SB having a convex waveform shown in the lower area of FIG. 5. As described above, the output voltage Vopa from the first operational amplifier 30 is input to the comparator 38 (see FIG. 4) and compared with the voltage Vcmp as the threshold value. When the output voltage Vopa from the first operational amplifier 30 is larger than the voltage Vcmp, the comparator 38 outputs the signal VS. When the output voltage Vopa from the first operational amplifier 30 is smaller than the voltage Vcmp, the comparator 38 stops outputting the signal VS. As a result, a rectangular wave RB converted from the wave SB having the convex waveform by the comparator 38 is input to the arithmetic unit 7.

The arithmetic unit 7 detects a point of time Te when the signal VS is output from the comparator 38 and a point of time Tf when the outputting of the signal VS is stopped. Specifically, the point of time Te is a detection starting point of time when the arithmetic unit 7 starts detecting of the passage of indenter 2 at the second optical sensor 25, and the point of time Tf is a detection ending point of time when the arithmetic unit 7 ends detecting of the passage of indenter 2 at the second optical sensor 25. Further, the arithmetic unit 7 calculates a time Th by halving a time Tg taken after the point of time Te has been detected until the point of time Tf is detected. The time Tg corresponds to a time during which the arithmetic unit 7 is detecting the passage of indenter 2 at the second optical sensor 25.

The arithmetic unit 7 determines the time between the point of time Td and the point of time Th, as a passage time T1 taken after the indenter 2 has passed the first optical sensor 24 until the indenter 2 passes the second optical sensor 25. In addition, the arithmetic unit 7 calculates the rebound speed of the indenter 2 by dividing the distance between the first optical sensor 24 and the second optical sensor 25 by the passage time T1.

In the present embodiment, the time between the point of time Td and the point of time Th is used as the passage time T1 taken after the indenter 2 has passed the first optical sensor 24 until the indenter 2 passes the second optical sensor 25. In a case where the time between the point of time Td and the point of time Th is used as the passage time T1, it is possible to make a measurement error of the passage time T1 smaller compared with a case where the time between the point of time Ta and the point of time Te is used as the passage time, so that a more correct rebound speed can be calculated.

The impact speed of the indenter 2 is calculated by the arithmetic unit 7, using a similar method. Specifically, the arithmetic unit 7 calculates the impact speed by determining the passage time taken after the indenter 2 has passed the second optical sensor 25 until the indenter 2 passes the first optical sensor 24. The arithmetic unit 7 also calculates the coefficient of restitution which represents the ratio of the rebound speed to the impact speed.

Although not shown, the second optical sensor 25 may be omitted, and thus the arithmetic unit 7 may calculate the impact speed and the rebound speed of the indenter 2, using only the first optical sensor 24. For example, the arithmetic unit 7 may calculate the rebound speed of the indenter 2 by dividing the diameter of the indenter 2 by the time Tc between the point of time Ta (i.e., the detection starting point of time of the indenter 2 at the first optical sensor 24) and the point of time Tb (i.e., the detection ending point of time of the indenter 2 at the first optical sensor 24) in FIG. 5. Similarly, the arithmetic unit 7 can calculate the impact speed of the indenter 2, using only the first optical sensor 24.

In the case where the impact speed and the rebound speed of the indenter 2 are measured by using only the first optical sensor 24, the size of the speed measuring body 23 can be reduced. Furthermore, since the first optical sensor 24 can be disposed near the surface of the specimen 8, it is possible to measure a correct coefficient of restitution.

As shown in FIG. 1, the holder 3 is inserted from the front end toward back end of the inner cylinder 13. The outer cylinder 12 has an outer cylinder flange 12c projecting radially outwardly of the outer cylinder 12, and the inner cylinder 13 has an inner cylinder flange 13c projecting radially outwardly of the inner cylinder 13. A holder flange member 40 is fixed to the outer circumferential surface of the holder 3. The holder flange member 40 includes a cylindrical static part 40a which is fixed to the outer circumferential surface of the holder 3 at its back end, and a projecting flange 40b which projects from the static part 40a radially outwardly of the holder 3. The inner cylinder 13 has a second elongated hole 13d passing through a side wall of the inner cylinder 13 and extending along a longitudinal direction of the inner cylinder 13. The projecting flange 40b of the holder flange member 40 extends through the second elongated hole 13d and projects outwardly of the outer circumferential surface of the inner cylinder 13.

The apparatus 1 for measuring coefficient of restitution has a first return spring 43 disposed between the inner cylinder flange 13c and the outer cylinder flange 12c, and the first return spring 43 biases the inner cylinder flange 13c in a direction away from the outer cylinder flange 12c. Further, the apparatus 1 for measuring coefficient of restitution has a second return spring 44 disposed between the projecting flange 40b and the outer cylinder flange 12c, and the second return spring 44 biases the projecting flange 40b in a direction away from the outer cylinder flange 12c. A first guide rod 46 is fixed to the outer cylinder flange 12c, the first guide rod 46 extending through a first through hole 40c formed in the projecting flange 40b to pass through the projecting flange 40b. The first guide rod 46 extends through the inside of the second return spring 44. An anchor 48 is fixed to the first guide rod 46 for restricting the projecting flange 40b to move in a direction away from the outer cylinder flange 12c by a biasing force of the second return spring 44. A second guide rod 47 is fixed to the inner cylinder flange 13c, the second guide rod 47 extending through a second through hole 40d formed in the projecting flange 40b to pass through the projecting flange 40b.

The outer cylinder flange 12c of the outer cylinder 12, the first guide rod 46, the second return spring 44, the holder flange member 40, and the anchor 48 constitutes a coupling mechanism 39 for coupling the holder 3 to the outer cylinder 12.

Figure 6:
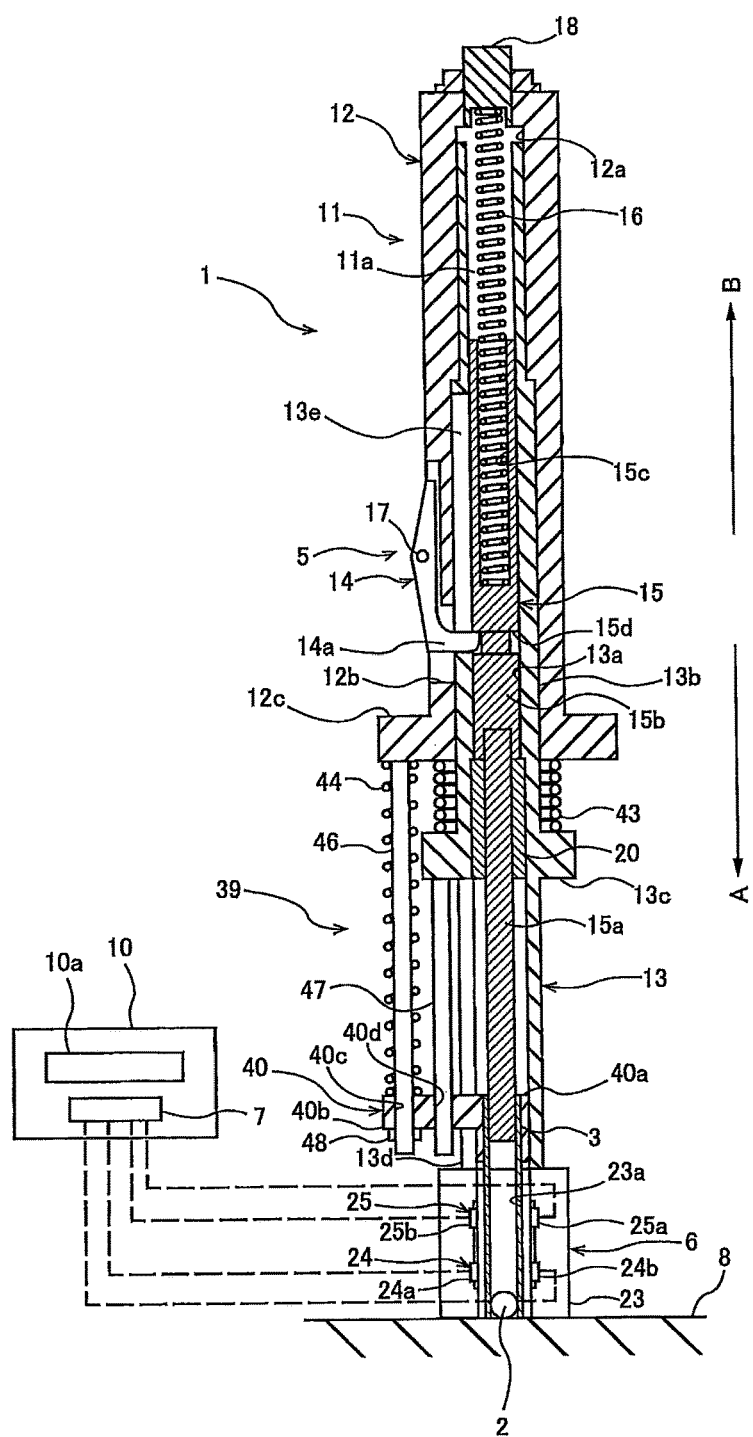
FIG. 6 is a schematic view showing a state in which the indenter is held in the holder again after a coefficient of restitution has been measured.

FIG. 6 is a schematic view showing a state in which the indenter 2 is held in the holder 3 again after the coefficient of restitution has been measured. As shown in FIG. 6, in order to hold the indenter 2 in the holder 3 again, an operator pushes the outer cylinder 12 toward the inner cylinder 13 against the biasing force of the first return spring 43 until the hook 14a of the ejection lever 14 engages with the groove 15d formed on the outer surface of the striker 15. At this time, the holder 3 that is coupled to the outer cylinder 12 by the coupling mechanism 39 moves forwards in the indenter channel 23a of the speed measuring unit 6. Since the projecting flange 40b of the holder flange member 40 can move along the second elongated hole 13d formed in the side wall of the inner cylinder 12, the holder flange member 40 can also move in the forward direction of the apparatus 1 for measuring coefficient of restitution. Since the second return spring 44 applies its biasing force to the flange holder member 40 fixed to the holder 3, the holder 3 moves in the forward direction of the apparatus 1 for coefficient of restitution while the distance between the holder 3 and the outer cylinder 12 is maintained. The holder 3 moving in the forward direction of the apparatus 1 for coefficient of restitution moves forwards in the indenter channel 23a formed in the speed measuring body 23 of the speed measuring unit 6 to reach the front end of the indenter channel 23a, and as a result, the indenter 2 is held in the front end of the holder 3.

When the outer cylinder 12 is pushed in the inner cylinder 13, the striker 15 is unable to move, because movement of the striker 15 in the forward direction of the apparatus 1 for measuring coefficient of restitution is restricted by the stopper 20. On the other hand, the biasing spring 16 is compressed. The hook 14a of the ejection lever 14 fixed to the outer cylinder 12 moves along the first elongated hole 13e formed in the side wall of the inner cylinder 12, and engages with the groove 13d formed on the outer surface of the striker 15. When the pushing force for pushing the outer cylinder 12 toward the inner cylinder 13 is removed, the outer cylinder 12 moves in the backward direction of the apparatus 1 for measuring coefficient of restitution by the biasing force of the first return spring 43. At this time, the striker 15, with which the hook 14a engages, also moves in the backward direction, and thus the striker 15 waits in the ejection position shown in FIG. 1.

When the outer cylinder 12 is pushed in the inner cylinder 13, the holder 3 is guided by the first guide rod 46. Similarly, when the outer cylinder 12 is pushed in the inner cylinder 13, the holder 3 is guided by the second guide rod 47. Therefore, the holder 3 is prevented from rotating with respect to the outer cylinder 12 and the inner cylinder 13.

With these configurations, the indenter 2 can be held in the holder 3 again by a simple operation in which the outer cylinder 12 is pushed in the inner cylinder 13. Accordingly, a burden on the operator can be reduced when the coefficients of restitution are to be measured successively.

According to the apparatus 1 for measuring coefficient of restitution, of this embodiment, an impactor (object) that impacts against the specimen 8 for measuring the coefficient of restitution is only the spherical indenter 2. Unlike the hammer for use in the Shore hardness test and the impact body for use in the Leeb hardness test, the impactor that impacts against the specimen 8 does not include an indenter support to which the indenter 2 would be fixed. As a result, since the mass of the impactor (object) that impacts against with the specimen 8 is greatly reduced, the mass effect occurring when the coefficient of restitution is to be measured is greatly reduced, thereby enabling the coefficient of restitution of the specimen to be correctly measured. The spherical indenter 2 is held in the holder 3, and ejected from the holder 3 toward the specimen 8 by the ejection mechanism 5. Therefore, since there is no limitation on the direction in which the indenter 2 is ejected, the test can be performed in a free direction. Furthermore, according to the apparatus 1 for measuring coefficient of restitution of this embodiment, the impact speed can be easily adjusted by moving the plug 18 forwards or backwards with respect to the outer cylinder 12.

The apparatus 1 for measuring coefficient of restitution according to the present embodiment, which is capable of greatly reducing the mass effect and performing the tests in a free direction, can measure coefficients of restitution of various specimens 8. For example, not only coefficients of restitution of metal materials, but also coefficients of restitution of foods such as chocolate and dried bonito or coefficients of restitution of non-metal materials such as ceramics, marble, and glass, can be measured. Further, the impactor that impacts against the specimen 8 is only the spherical indenter 2, and thus has a very small volume. Therefore, the heat capacity of the impactor is small. The indenter 2 contacts the specimen 8 instantaneously. As a result, the coefficient of restitution of a specimen 8 which is of high or low temperature can be correctly measured, because the amount of change in a surface temperature of the specimen due to the test is greatly reduced.

The apparatus 1 for measuring coefficient of restitution according to the present embodiment can use indenters 2 having various diameters by appropriately selecting a size of the holder 3 and a diameter of the striker body 15a depending on the diameter of the indenter 2. Therefore, the apparatus 1 for measuring coefficient of restitution according to the present embodiment can use an indenter 2 having a very small diameter, so that the mass effect can further be reduced.

From the viewpoint of reducing the mass effect that occur when the test is performed, it is preferable to use an indenter 2 having as small a diameter as possible. In contrast, when the coefficient of restitution of a specimen 8 which has small irregularities on its surface is measured, the direction in which the indenter 2 is rebounded from the specimen 8 may greatly deviate from (be inclined with respect to) the direction in which the indenter 2 is ejected from the ejection mechanism 5. The reason of this is that the diameter of the indenter 2 is too small with respect to the size of the irregularities formed on the surface of the specimen 8. Therefore, in order to stabilize the direction in which the indenter 2 is rebound, while reducing the occurrence of the mass effect, it is preferable that the diameter of the indenter 2 is equal to or less than 5 mm.

As the diameter of the indenter 2 decreases, the burden on the operator for measuring the coefficient of restitution increases. For example, when the indenter 2 having a very small diameter is used, the operator is likely to lose the indenter 2. Therefore, from the viewpoint of working efficiency, it is preferable that the diameter of the indenter 2 is equal to or more than 0.5 mm. Furthermore, in order to reliably confirm a fracture or defect of the indenter 2 prior to the measurement of the coefficient of restitution, it is more preferable that the diameter of the indenter 2 is equal to or more than 2 mm. More specifically, the diameter of the indenter 2 is preferably in the range from 0.5 mm to 5 mm, and more preferably in the range from 2 mm to 5 mm.

The speed measuring unit 6 of the apparatus 1 for measuring coefficient of restitution according to this embodiment measures the impact speed and the rebound speed of the indenter 2 using the optical sensors 24, 25. Therefore, there is no limitation on the material of the indenter 2, and the indenter 2 may be made of a metal material such as cemented carbide or the like, or a non-metal material such as ceramics, diamond, or the like. Preferably, the indenter 2 is a bearing ball made of alumina which is ceramics. Since the bearing ball made of alumina has high sphericity, the apparatus 1 for measuring coefficient of restitution can measure correct coefficients of restitution with high repeatability. The bearing ball made of alumina is inexpensive and easily commercially available.

Figure 7:
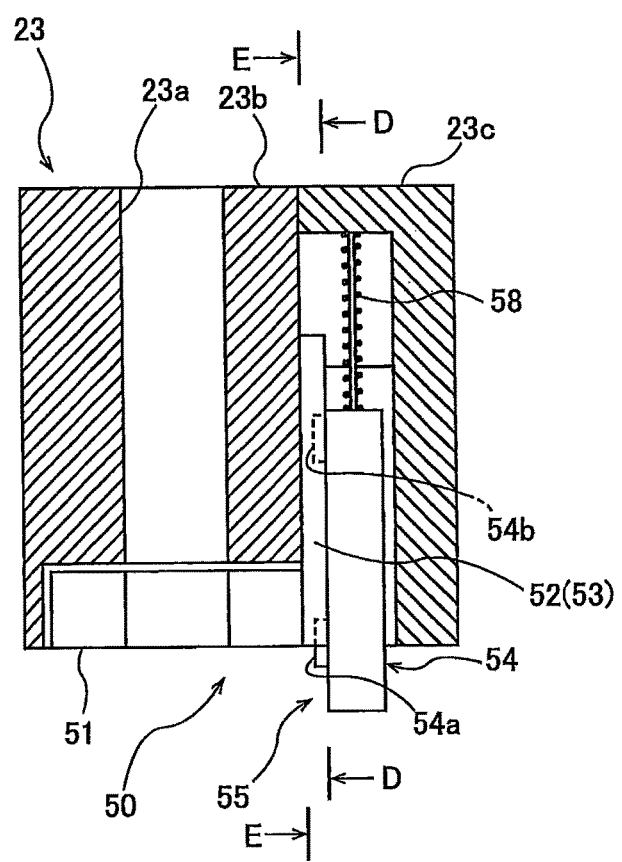
FIG. 7 is a schematic cross-sectional view showing an example of a speed measuring body that is provided with a shutter mechanism.

The speed measuring body 23 of the speed measuring unit 6 may have a shutter mechanism 50 which opens the opening of the indenter channel 23a in the speed measuring body 23 when the speed measuring unit 6 contacts the specimen 8, and which closes the opening of the indenter channel 23a in the speed measuring body 23 when the speed measuring unit 6 is separated from the specimen 8. FIG. 7 is a schematic cross-sectional view showing an example of the speed measuring body 23 that is provided with the shutter mechanism 50. As shown in FIG. 7, the shutter mechanism 50 of this embodiment includes a door 51 disposed at the opening of the indenter channel 23a, an opening/closing rod 54 whose front end projects from the speed measuring body 23, and a link mechanism 55 for converting movement of the opening/closing rod 54 into opening/closing movement of the door 51. The speed measuring body 23 of this embodiment is constructed by a first member 23b in which the indenter channel 23a is formed and the door 51 is disposed, and a second member 23c in which the opening/closing rod 54 is disposed.

Figure 8A:
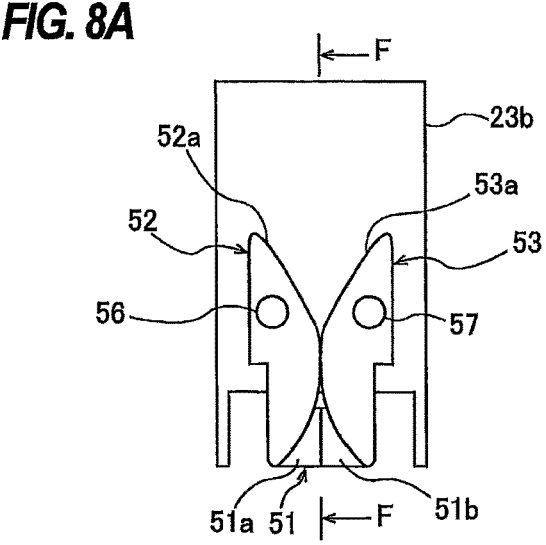
FIG. 8A is a view as viewed along arrows D in FIG. 7.
Figure 8B:
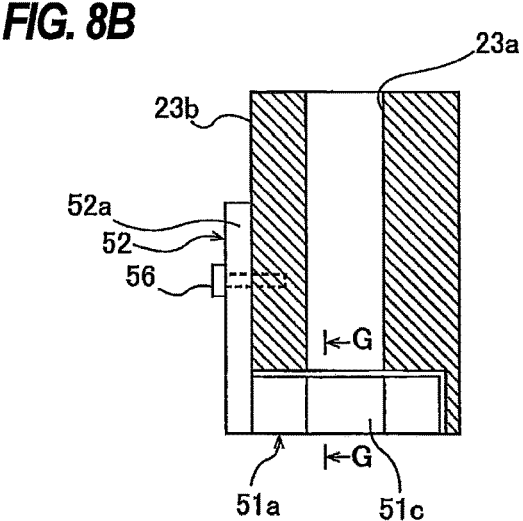
FIG. 8B is a cross-sectional view taken along line F-F of FIG. 8A.
Figure 8C:
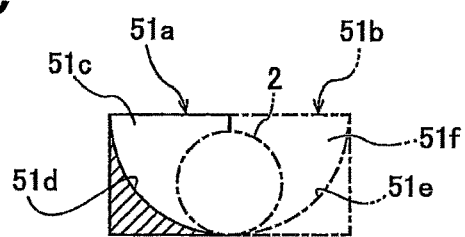
FIG. 8C is a cross-sectional view taken along line G-G of FIG. 8B.

FIG. 8A is a view as viewed along arrows D in FIG. 7, FIG. 8B is a cross-sectional view taken along line F-F of FIG. 8A, and FIG. 8C is a cross-sectional view taken along line G-G of FIG. 8B. As shown in FIG. 8A, the door 51 of this embodiment has a first door 51a and a second door 51b which open and close the opening of the indenter channel 23a in the speed measuring body 23 by the link mechanism 55. The link mechanism 55 will be described later. When the first door 51a and the second door 51b abut against each other, the opening of the indenter channel 23a is closed, and when the first door 51a and the second door 51b are separated from each other, the opening of the indenter channel 23a is opened. FIG. 8A illustrates a state in which the first door 51a and the second door 51b abut against each other, and thus the opening of the indenter channel 23a is closed.

As shown in FIGS. 8A and 8B, a first opening/closing guide 52 having a first arc-shaped surface 52a is fixed to a side surface of the first door 51a, and a second opening/closing guide 53 having a second arc-shaped surface 53a is fixed to a side surface of the second door 51b. The first arc-shaped surface 52a of the first opening/closing guide 52 and the second arc-shaped surface 53a of the second opening/closing guide 53 face each other. The first opening/closing guide 52 is pivotably secured to the first member 23b by a first opening/closing shaft 56. In other words, the first opening/closing guide 52 can pivot about the first opening/closing shaft 56, and as a result, the first door 51a fixed to the first opening/closing guide 52 can pivot about the first opening/closing shaft 56. The second opening/closing guide 53 is pivotably secured to the first member 23b by a second opening/closing shaft 57. In other words, the second opening/closing guide 53 can pivot about the second opening/closing shaft 57, and as a result, the second door 51b fixed to the second opening/closing guide 53 can pivot about the second opening/closing shaft 57.

As shown in FIGS. 8B and 8C, in a central region of the first door 51a, a first receiving portion 51c (see FIG. 8B) is formed, in which a first sloping surface 51d with a circular-arc-shape is formed. In a central region of the second door 51b also, which is illustrated by the imaginary lines (dot-and-dash lines) in FIG. 8C, a second receiving portion 51f is formed, in which a second sloping surface 51e with a circular-arc shape is formed. When the first door 51a and the second door 51b abut against each other, the indenter 2 can be housed in an internal space formed by the first receiving portion 51c and the second receiving portion 51f.

Figure 9A:
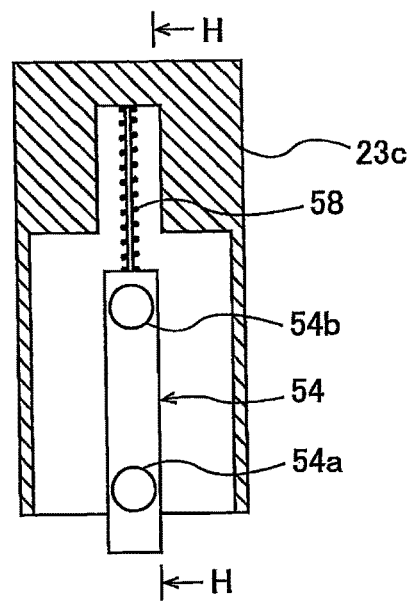
FIG. 9A is a view as viewed along arrows E in FIG. 7.
Figure 9B:
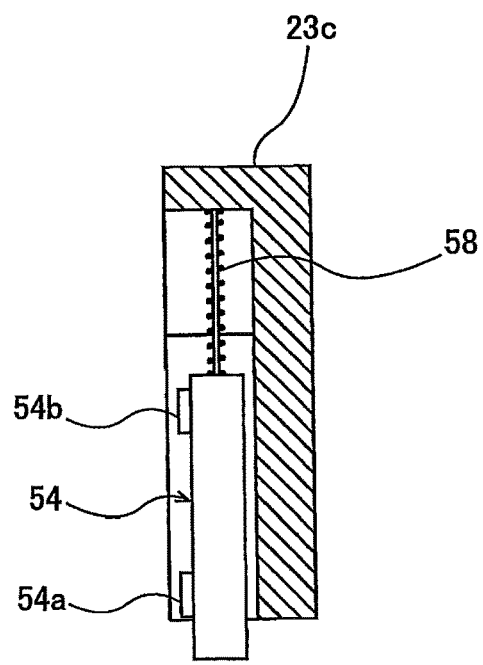
FIG. 9B is a cross-sectional view taken along line H-H of FIG. 9A.

FIG. 9A is a view as viewed along arrows E in FIG. 7, and FIG. 9B is a cross-sectional view taken along line H-H of FIG. 9A. As shown in FIG. 9A, one end of an opening/closing spring 58 is fixed to the back end of the opening/closing rod 54, and the other end of the opening/closing spring 58 is fixed to the second member 23c. In this state, the front end of the opening/closing rod 54 projects forwards from the front end of the second member 23c. As shown in FIGS. 9A and 9B, a first protrusion 54a and a second protrusion 54b, which are cylindrical in shape, are formed on a side surface of the opening/closing rod 54. The first protrusion 54a is positioned forwardly of the second protrusion 54b on the opening/closing rod 54. The first protrusion 54a and the second protrusion 54b project from the side surface of the opening/closing rod 54 toward the first member 23b.

Figure 10:
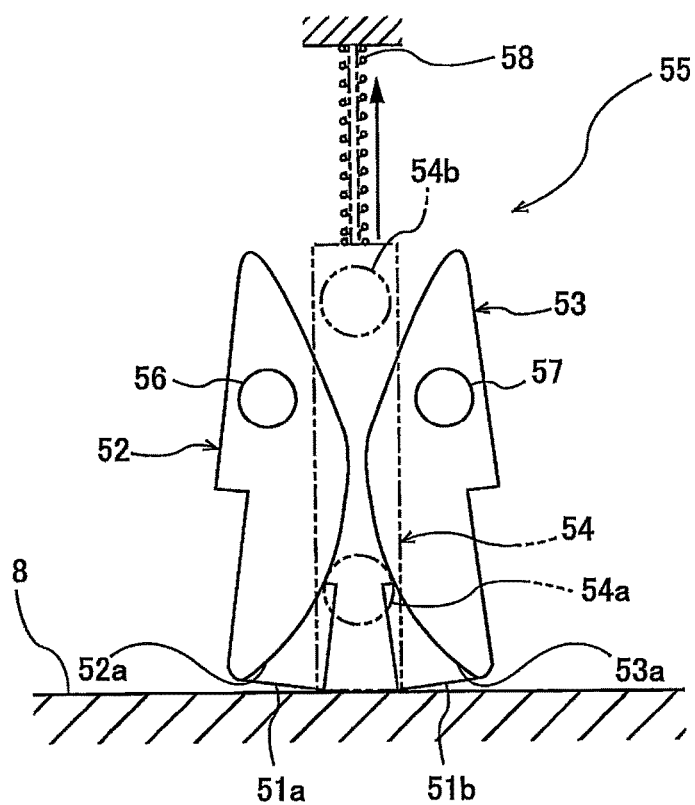
FIG. 10 is a schematic view showing a state in which a first door and a second door are pivoted in directions away from each other by a link mechanism, and thus an opening of an indenter channel is opened.
Figure 11:
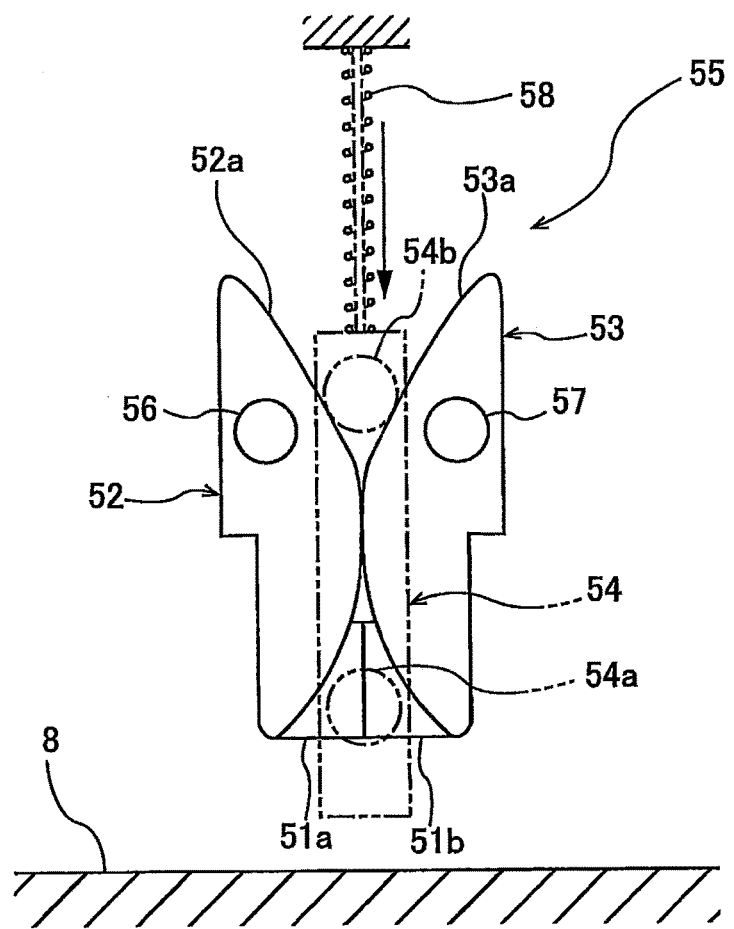
FIG. 11 is a schematic view showing a state in which the first door and the second door are brought into abutment against each other by the link mechanism, and thus the opening of the indenter channel is closed.

The link mechanism 55 of the shutter mechanism 50 is constructed by the first opening/closing guide 52, the second opening/closing guide 53, the first protrusion 54a and the second protrusion 54b formed on the opening/closing rod 54, and the opening/closing spring 58. FIG. 10 is a schematic view showing a state in which the first door 51a and the second door 51b are pivoted in directions away from each other by the link mechanism 55, and thus the opening of the indenter channel 23a is opened. FIG. 11 is a schematic view showing a state in which the first door 51a and the second door 51b are brought into abutment against each other by the link mechanism 55, and thus the opening of the indenter channel 23a is closed.

As shown in FIG. 10, when the speed measuring body 23 of the speed measuring unit 6 is brought into contact with the surface of the specimen 8, the opening/closing rod 54 is pushed in against the biasing force of the opening/closing spring 58, until a front end of the opening/closing rod 54 is housed into the speed measuring body 23. At this time, the first protrusion 54a formed on the opening/closing rod 54 contacts the first arc-shaped surface 52a of the first opening/closing guide 52 and the second arc-shaped surface 53a of the second opening/closing guide 53, thereby rotating the first opening/closing guide 52 and the second opening/closing guide 53 respectively, about the first opening/closing shaft 56 and the second opening/closing shaft 57 in directions to separate the first door 51a and the second door 51b away from each other. As a result, the opening of the indenter channel 23a of the speed measuring body 23 is opened, allowing the indenter 2 to impact against the surface of the specimen 8.

As shown in FIG. 11, when the speed measuring body 23 of the speed measuring unit 6 is spaced from the surface of the specimen 8, the opening/closing rod 54 moves forwards until the front end of the opening/closing rod 54 projects from the front end of the speed measuring body 23 with the spring force of the opening/closing spring 58. At this time, the second protrusion 54b formed on the opening/closing rod 54 contacts the first arc-shaped surface 52a of the first opening/closing guide 52 and the second arc-shaped surface 53a of the second opening/closing guide 53, thereby rotating the first opening/closing guide 52 and the second opening/closing guide 53 respectively, about the first opening/closing shaft 56 and the second opening/closing shaft 57 in directions to bring the first door 51a and the second door 51b into abutment against each other. As a result, the opening of the indenter channel 23a of the speed measuring body 23 is closed, housing the indenter 2 in the internal space formed by the first receiving portion 51c and the second receiving portion 51f (see FIG. 8C). At this time, the indenter 2 is guided by the first sloping surface 51d of the first receiving portion 51c and the second sloping surface 51e of the second receiving portion 51f, preventing the indenter 2 from being pinched by the first door 51a and the second door 51b.

According to the shutter mechanism 50 of this embodiment, the opening of the indenter channel 23a is opened, only when the speed measuring body 23 contacts the specimen 8. On the other hand, when the speed measuring body 23 is spaced from the specimen 8, the opening of the indenter channel 23a is closed. Therefore, a loss of the indenter 2 ejected from the ejection mechanism 5 is effectively prevented, so that the burden on the operator can be reduced.

Figure 12:
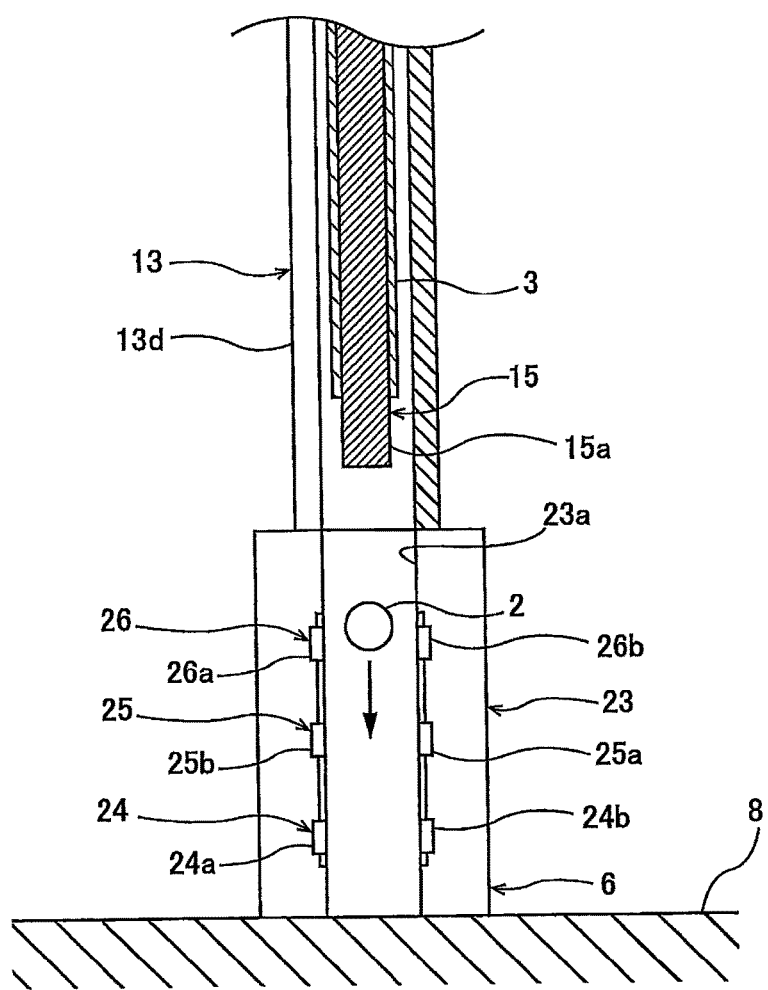
FIG. 12 is a schematic view showing the speed measuring unit according to another embodiment.

FIG. 12 is a schematic view showing the speed measuring unit 6 according to another embodiment. The speed measuring unit 6 shown in FIG. 12 has a third passage sensor 26 in addition to the first passage sensor 24 and the second passage sensor 25. As described above, the "passage sensor" collectively refers to sensors capable of detecting the passage of an object, and includes an optical sensor or a magnetic sensor, for example. The embodiment in which the first passage sensor 24, the second passage sensor 25, and the third passage sensor 26 are optical sensors, will be described below.

The first optical sensor 24, the second optical sensor 25, and the third optical sensor 26 are arrayed along the indenter channel 23a. The first optical sensor 24 is positioned forwardly of the second optical sensor 25 and the third optical sensor 26 in the speed measuring body 23, and the second optical sensor 25 is positioned forwardly of the third optical sensor 26 in the speed measuring body 23.

The third optical sensor 26 is identical in structure to the first optical sensor 24 and the second optical sensor 25. Specifically, the third optical sensor 26 has a third light emitter 26a for emitting light into the indenter channel 23a and a third light receiver 26b for receiving the light emitted from the third light emitter 26a. The third light emitter 26a is an LED, and the third light receiver 26b is a photodiode. The arrangement of an electric circuit of the third optical sensor 26 is identical to the arrangement of the electric circuit of the first optical sensor 24 described with reference to FIG. 4. Specifically, the amount of light emitted from the third light emitter 26a can automatically be adjusted so that the voltage Vopa output from the first operational amplifier 30 in the electric circuit of the third optical sensor 26 converges on the preset base voltage Vdet at all times.

The apparatus 1 for measuring coefficient of restitution 1 according to the embodiments described herein are able to perform tests in free directions. For example, the indenter 2 can be ejected upwardly or downwardly. If the indenter 2 is ejected in different directions, gravitational forces in different directions act on the indenter 2. Therefore, depending on the direction in which the ejected indenter 2 is ejected, small errors may be produced in the measured coefficients of restitution. In particular, the gravitational force tends to have a greater effect when the impact speed and the rebound speed of the indenter 2 are low. Accordingly, it is preferable to calculate the coefficient of restitution using, as the impact speed, the speed of the indenter 2 at the instant at which the indenter 2 impacts against the surface of the specimen 8, and using, as the rebound speed, the speed of the indenter 2 at the instant at which the indenter 2 is rebounded from the surface of the specimen 8. A method of determining, through calculations, the impact speed of the indenter 2 at the instant at which the indenter 2 impacts against the specimen 8, and the rebound speed of the indenter 2 at the instant at which the indenter 2 is rebound from the specimen 8 will be described below with reference to FIG. 13.

Figure 13:
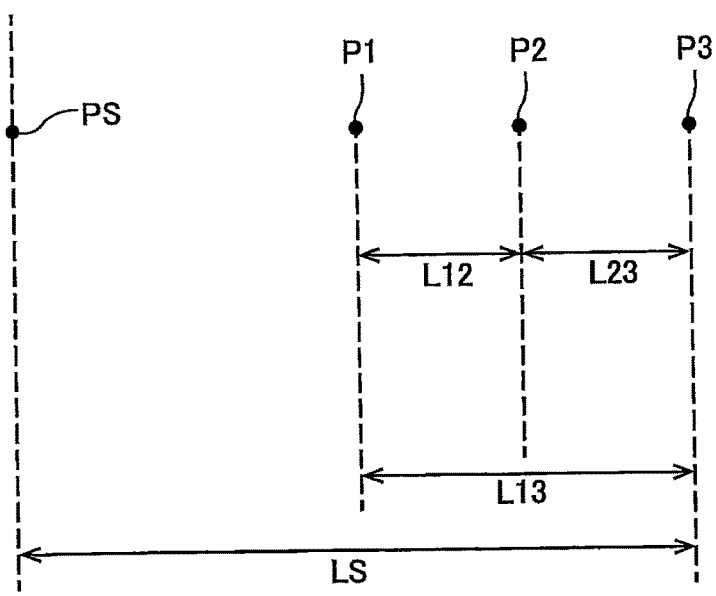
FIG. 13 is an explanatory diagram illustrating a method of determining, through calculations, the impact speed at the instant at which the indenter impacts against a surface of the specimen, and the rebound speed at the instant at which the indenter is rebounded from the specimen.

FIG. 13 is an explanatory diagram illustrating a method of determining, through calculations, the impact speed of the indenter 2 at the instant at which the indenter 2 impacts against the surface of the specimen 8 and the rebound speed of the indenter 2 at the instant at which the indenter 2 is rebounded from the specimen 8. In FIG. 13, a point Ps represents the surface of the specimen 8, a point P1 represents the position of the first optical sensor 24, a point P2 represents the position of the second optical sensor 25, and a point P3 represents the position of the third optical sensor 26. A method of calculating the impact speed of the indenter 2 at the instant at which the indenter 2 reaches the point Ps after passing the point P3, the point P2, and the point P1 in this order, will be described below.

The speed of the indenter 2 passing the point P3 (i.e., the third optical sensor 26) is represented by v3, the speed of the indenter 2 passing the point P2 (i.e., the second optical sensor 25) is represented by v2, the speed of the indenter 2 passing the point P1 (i.e., the first optical sensor 24) is represented by v1, and the speed of the indenter 2 at the instant at which the indenter 2 reaches the point Ps (i.e., the surface of the specimen 8) is represented by vs. Furthermore, the average speed between the point P3 and the point P2 is represented by v23, the average speed between the point P2 and the point P1 is represented by v12, and the average speed between the point P3 and the point P1 is represented by v13. A distance from the point P3 to the point P2 is represented by L23, a distance from the point P2 to the point P1 is represented by L12, a distance from the point P3 to the point P1 is represented by L13, and a distance from the point P3 to the point Ps is represented by Ls. The controller 7 measures, according to the method described with reference to FIG. 5, a time T23 taken after the indenter 2 has passed the point P3 until it passes the point P2, a time T12 taken after the indenter 2 has passed the point P2 until it passes the point P1, and a time T13 taken after the indenter 2 has passed the point P3 until it passes the point P1.

The average speed v23 between the point P3 and the point P2 can be calculated from the time T23 measured by the controller 7 and the known L23 according to the following equation (1).

$$v23 = L23/T23 \quad (1)$$

Similarly, the average speed v12 can be calculated according to the following equation (2), and the average speed v13 can be calculated according to the following equation (3).

$$v12 = L12/T12 \quad (2)$$

$$v13 = L13/T13 \quad (3)$$

Assuming that the indenter 2 is making uniformly accelerated motion at an acceleration $\alpha$, the speed v23, the speed v2, and the speed v3 satisfy the relationship according to the following equation (4).

$$v23 = (v2+v3)/2 \quad (4)$$

Similarly, the speed v12, the speed v1, and the speed v2 satisfy the relationship according to the following equation (5), and the speed v13, the speed v1, and the speed v3 satisfy the relationship according to the following equation (6).

$$v12 = (v1+v2)/2 \quad (5)$$

$$v13 = (v1+v3)/2 \quad (6)$$

From the equation (4), the equation (5), and the equation (6), the following equation (7), equation (8), and equation (9) are obtained.

$$v1 = -v23 + v12 + v13 \quad (7)$$

$$v2 = v23 + v12 - v13 \quad (8)$$

$$v3 = v23 - v12 + v13 \quad (9)$$

The acceleration $\alpha$ of the indenter 2 can be determined according to the following equation (10).

$$\alpha = (v1-v3)/T13 \quad (10)$$

Since the arithmetic unit 7 has obtained the speed v23, the speed v12, and the speed v13 according to the above-described equations (1), (2), (3), the arithmetic unit 7 can calculate the speed v1, the speed v2, and the speed v3 according to the equation (7), the equation (8), and the equation (9). As a result, the arithmetic unit 7 can calculate the acceleration $\alpha$ of the indenter 2 according to the equation (10).

If it is assumed that the indenter 2 is making uniformly accelerated motion at the acceleration $\alpha$, the impact speed vs at the instant at which the indenter 2 impacts against the point Ps (i.e., the surface of the specimen 8) can be determined from the following equation (11) or equation (12).

$$vs = (v3^2 + 2Ls \cdot \alpha)^{1/2} \quad (11)$$

$$vs = v3 \cdot (1 + ((v1/v3)^2 - 1)(Ls/L13)))^{1/2} \quad (12)$$

As described above, since the arithmetic unit 7 has obtained the speed v3, the speed v2, the speed v1, and the acceleration $\alpha$ through calculations, and the distance Ls and the distance L13 are known, the arithmetic unit 7 can calculate the impact speed vs at the instant at which the indenter 2 impacts against the surface of the specimen 8.

Next, a method of determining, through calculations, the rebound speed at the instant at which the indenter 2 is rebounded from the surface of the specimen 8 will be described below with reference to FIG. 13. In FIG. 13, the point Ps represents the surface of the specimen 8, the point P1 represents the position of the first optical sensor 24, the point P2 represents the position of the second optical sensor 25, and the point P3 represents the position of the third optical sensor 26. The indenter 2 which has been rebounded from the surface of the specimen 8 passes the point P1, the point P2, and the point P3 in this order.

The speed of the indenter 2 passing the point P1 (i.e., the first optical sensor 24) after being rebounded from the point Ps is represented by v1', the speed of the indenter 2 passing the point P2 (i.e., the second optical sensor 25) after being rebounded from the point Ps is represented by v2', and the speed of the indenter 2 passing the point P3 (i.e., the third optical sensor 26) after being rebounded from the point Ps is represented by v3'. Furthermore, the average speed between the point P1 and the point P2 is represented by v12', the average speed between the point P2 and the point P3 is represented by v23', and the average speed between the point P1 and the point P3 is represented by v13'. The distance from the point P1 to the point P2 is represented by L12, the distance from the point P2 to the point P3 is represented by L23, the distance from the point P1 to the point P3 is represented by L13, and the distance from the point Ps to the point P3 is represented by Ls. The controller 7 measures, according to the method described with reference to FIG. 5, a time T12' taken after the indenter 2 rebounded from the point Ps has passed the point P1 until it passes the point P2, a time T23' taken after the indenter 2 rebounded from the point Ps has passed the point P2 until it passes the point P3, and a time T13' taken after the indenter 2 rebounded from the point Ps has passed the point P1 until it passes the point P3.

The average speed v12' between the point P1 and the point P2 can be calculated from the time T12' measured by the controller 7 and the known L12 according to the following equation (13).

$$v12' = L12/T12' \quad (13)$$

Similarly, the average speed v23' can be calculated according to the following equation (14), and the average speed v13' can be calculated according to the following equation (15).

$$v23' = L23/T23' \quad (14)$$

$$v13' = L13/T13' \quad (15)$$

Assuming that the indenter 2 is making uniformly accelerated motion at an acceleration $\alpha'$, the speed v12', the speed v1', and the speed v2' satisfy the relationship according to the following equation (16).

$$v12' = (v1'+v2')/2 \quad (16)$$

Similarly, the speed v23', the speed v2', and the speed v3' satisfy the relationship according to the following equation (17), and the speed v13', the speed v1', and the speed v3' satisfy the relationship according to the following equation (18).

$$v23' = (v2'+v3')/2 \quad (17)$$

$$v13' = (v1'+v3')/2 \quad (18)$$

From the equation (16), the equation (17), and the equation (18), the following equation (19), equation (20), and equation (21) are obtained.

$$v1'=-v23'+v12'+v13' \quad (19)$$

$$v2'=v23'+v12'-v13' \quad (20)$$

$$v3'=v23'-v12'+v13' \quad (21)$$

The acceleration $\alpha'$ of the indenter 2 can be determined according to the following equation (22).

$$\alpha=(v3'-v1')/T13' \quad (22)$$

Since the arithmetic unit 7 has obtained the speed v12', the speed v23', and the speed v13' from the above-described equations (13), (14), and (15), the arithmetic unit 7 can calculate the speed v1', the speed v2', and the speed v3' according to the equation (19), the equation (20), and the equation (21). As a result, the arithmetic unit 7 can calculate the acceleration $\alpha'$ of the indenter 2 rebounded from the point Ps according to the equation (22).

If it is assumed that the indenter 2 is making uniformly accelerated motion at the acceleration $\alpha'$, the rebound speed vs' of the indenter 2 at the instance at which it has rebounded from the point Ps (i.e., the surface of the specimen 8) can be determined from the following equation (23) or equation (24).

$$vs'=(v1'^2+2Ls\cdot\alpha)^{1/2} \quad (23)$$

$$vs'=v1'\cdot(1+((v3'/v1')^2-1)\cdot((L13-Ls)/L13))^{1/2} \quad (24)$$

As described above, since the arithmetic unit 7 has obtained the speed v1', the speed v2', the speed v3', and the acceleration $\alpha'$ through calculations, and the distance Ls and the distance L13 are known, the arithmetic unit 7 can calculate the rebound speed vs' at the instance at which the indenter 2 is rebounded from the surface of the specimen 8.

In this manner, the arithmetic unit 7 is capable of determined, through calculations, the impact speed vs of the indenter 2 at the instant at which the indenter 2 impacts against the specimen 8, and the rebound speed vs' of the indenter 2 at the instant at which the indenter 2 is rebounded from the surface of the specimen 8. When the arithmetic unit 7 calculates the coefficient of restitution based on the impact speed vs at the instant at which the indenter 2 impacts against the specimen 8 and the rebound speed vs' at the instant at which the indenter 2 is rebounded from the surface of the specimen 8, the arithmetic unit 7 can obtain the coefficient of restitution in which the effect of the gravitational force acting on the indenter 2 is removed.

Figure 14:
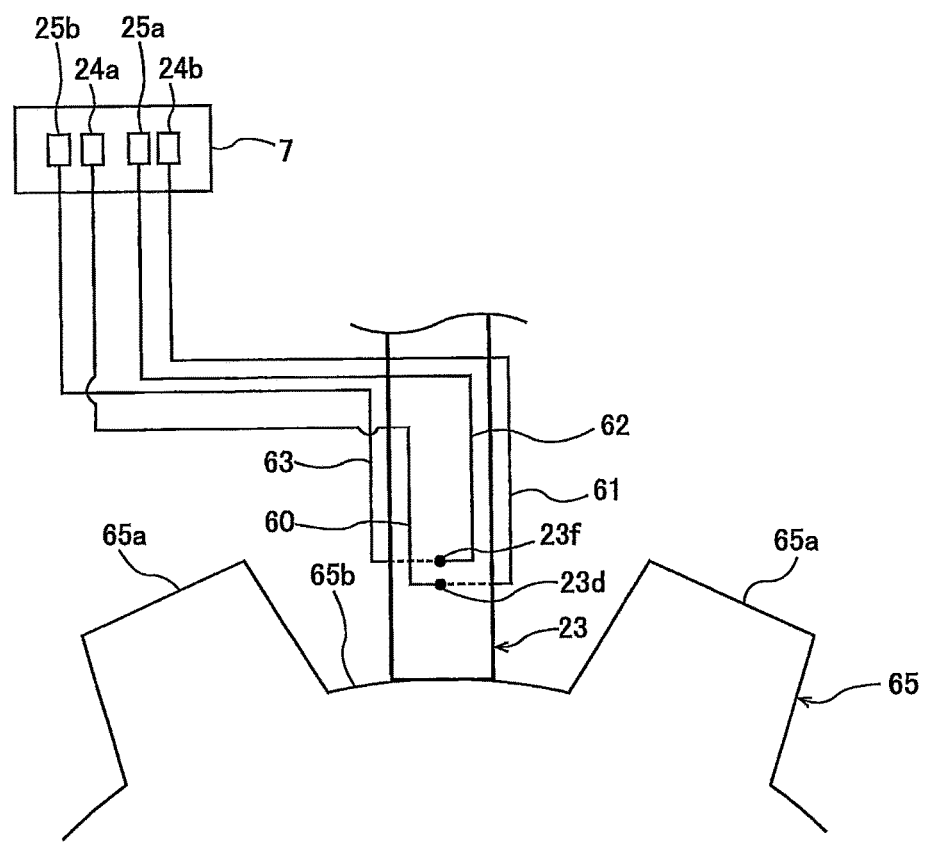
FIG. 14 is a schematic view showing the speed measuring unit according to still another embodiment.

FIG. 14 is a schematic view showing the speed measuring unit 6 according to still another embodiment. The first light emitter 24a and the first light receiver 24b of the first optical sensor 24, and the second light emitter 25a and the second light receiver 25b of the second optical sensor 25 of the speed measuring unit 6 shown in FIG. 14 are disposed in the arithmetic unit 7. In other words, the first optical sensor 24 and the second optical sensor 25 are disposed in the arithmetic unit 7. The speed measuring body 23 has four through holes 23d, 23e, 23f, and 23g formed therein, which extend from side faces of the speed measuring body 23 to wall surfaces of the indenter channel 23a. Although only the through holes 23d, 23f are illustrated in FIG. 14, the through hole 23e is formed in a position facing the through hole 23d, and the through hole 23g is formed in a position facing the through hole 23f.

A first optical fiber 60 extending from the first light emitter 24a is fitted in the through hole 23d, so that the light emitted by the first light emitter 24a passes through the first optical fiber 60 and is emitted into the indenter channel 23a. A second optical fiber 61 extending from the first light receiver 24b is fitted in the through hole 23e, so that the light emitted by the first light emitter 24a passes through the second optical fiber 61 and is received by the first light receiver 24b. In other words, the first light emitter 24a of the first optical sensor 24 emits the light through the first optical fiber 60 into the indenter channel 23a, and the first light receiver 24b of the first optical sensor 24 receives the light emitted into the indenter channel 23a through the second optical fiber 61. Similarly, a third optical fiber 62 extending from the second light emitter 25a is fitted in the through hole 23f, so that the light emitted by the second light emitter 25a passes through the third optical fiber 62 and is emitted into the indenter channel 23a. A fourth optical fiber 63 extending from the second light receiver 25b is fitted in the through hole 23g, so that the light emitted by the second light emitter 25a passes through the fourth optical fiber 63 and is received by the second light receiver 25b. In other words, the second light emitter 25a of the second optical sensor 25 emits the light through the third optical fiber 62 into the indenter channel 23a, and the second light receiver 25b of the second optical sensor 25 receives the light emitted into the indenter channel 23a through the fourth optical fiber 63.

According to the constructions shown in FIG. 14, the size of the speed measuring body 23 can be reduced. Therefore, the speed measuring body 23 can be inserted into a small gap. For example, as shown in FIG. 14, it is possible to measure the coefficient of restitution of a bottomland 65b formed between two adjacent teeth 65a, 65b of a gear 65.

Figure 15:
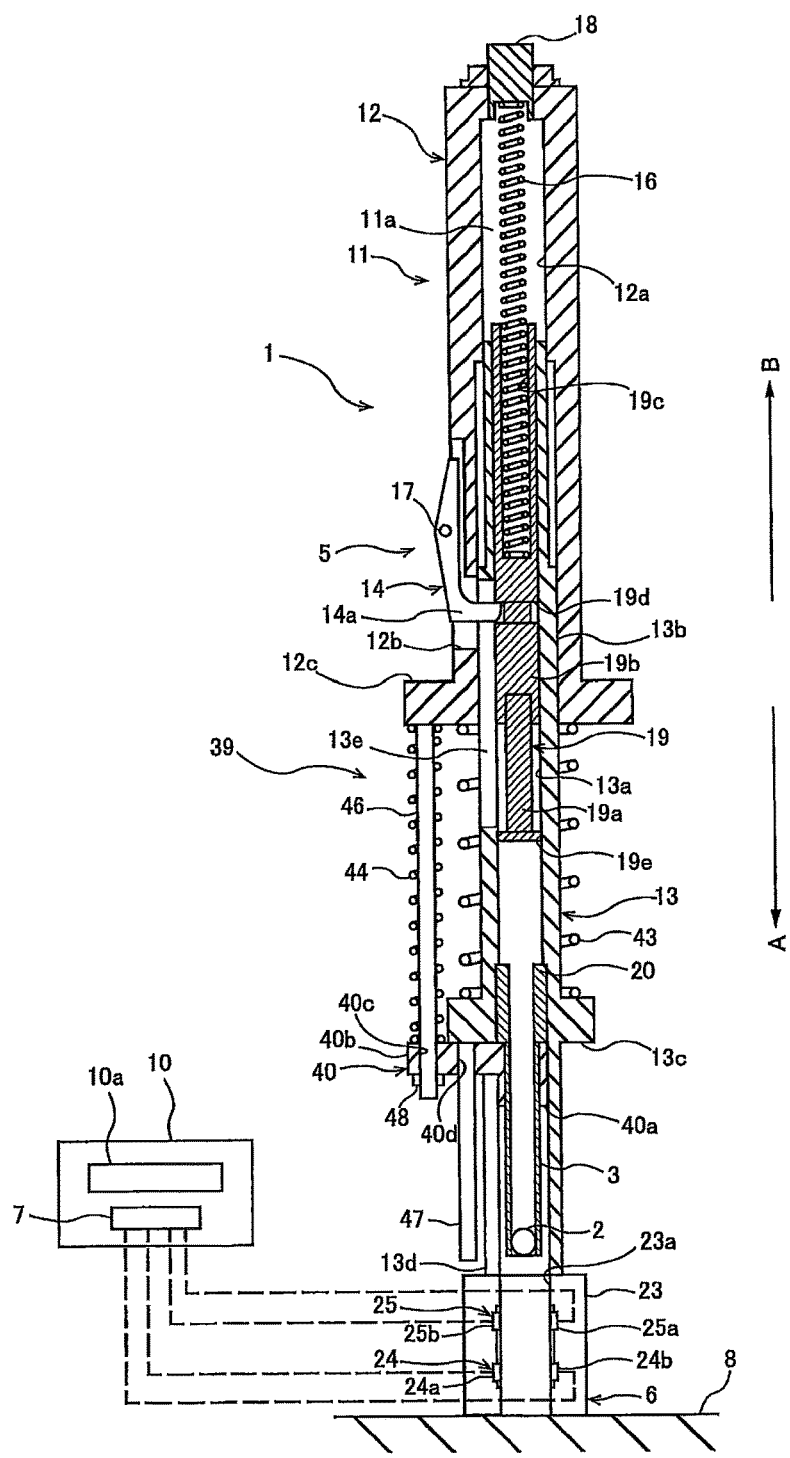
FIG. 15 is a schematic cross-sectional view showing the apparatus for measuring coefficient of restitution according to another embodiment.

FIG. 15 is a schematic cross-sectional view showing the apparatus 1 for measuring coefficient of restitution according to another embodiment. In the apparatus 1 for measuring coefficient of restitution shown in FIG. 15, instead of the striker 15 shown in FIG. 1, a piston rod 19 is used as an indenter pushing member. The piston rod 19 applies an air pressure to the indenter 2 held in the holder 3, ejecting the indenter 2 from the holder 3 toward the material 8 by use of this air pressure. Structures of the apparatus 1 for measuring coefficient of restitution according to the present embodiment other than the piston rod 19 are identical to those of the apparatus 1 for measuring coefficient of restitution described above, and their repetitive descriptions are omitted.

The piston rod 19 includes a cylindrical rod body 19a, a cylindrical rod support 19b having a diameter greater than the diameter of the rod body 19a, and a disk-shaped piston head 19e fixed to the front end of the rod body 19a. The rod body 19a has its back end embedded in the front end of the rod support 19b, so that the rod body 19a is fixed to the rod support 19b. The central axis of the rod body 19a is in alignment with the central axis of the body support 19b. The piston head 19e has its outer circumferential surface slidable against the inner circumferential surface of the inner cylinder 13. The central axis of the piston head 19e is in alignment with the central axis of the rod body 19a.

The front end of the biasing spring 16 is inserted into a guide hole 19c formed in the rod support 19b. The guide hole 19c extends from the back end toward front end of the rod support 19b, and the central axis of the guide hole 19c is in alignment with the central axis of the rod support 19b. To the back end of the outer cylinder 12, a plug 18 that closes the opening of the outer cylinder 12 is fixed, and the back end of the biasing spring 16 is supported by the plug 18. The plug 18 according to the present embodiment has a cylindrical shape, and the screw thread is formed on the outer circumferential surface of the plug 18. The opening formed on the back end of the outer cylinder 12 is constructed as the threaded hole into which the screw thread formed on the outer circumferential surface of the plug 18 is screwed. The screw thread formed on the plug 18 engages with the threaded hole, thereby securing the plug 18 to the outer cylinder 12. By rotating the plug 18, the plug 18 can be moved forwards or backwards relative to the outer cylinder 12. As a result, the biasing force applied to the piston rod 19 from the biasing spring 16 can be easily changed, because a length of the biasing spring 16 can be easily changed.

With these configurations, the biasing spring 16 is disposed between the outer cylinder 12 and the piston rod 19. As described above with reference to FIG. 6, the biasing spring 16 is compressed by movement of the outer cylinder 12, thereby allowing the biasing force to be applied to the piston rod 19. As shown in FIG. 15, when the biasing spring 16 is compressed, the biasing spring 16 applies the biasing force for moving the piston rod 19 in the forward direction of the ejection mechanism 5, to the piston rod 15. This position of the piston rod 19 is an ejection position of the piston rod 19.

An annular groove 19d extending along a circumferential direction of the rod support 19b is formed on the outer surface of the rod support 19b. The groove 19d may be formed on a part of the outer surface of the rod support 19b. The ejection lever 15 is fixed to the outer surface of the outer cylinder 12, the ejection lever 15 having the hook 14a that can engage with the groove 19d when the piston rod 19 is in the ejected position shown in FIG. 15. The ejection lever 14 has the through hole, and the rotational shaft 17 which is secured to a bracket (not shown) extending radially outwardly from the outer surface of the outer cylinder 12, is inserted into this through hole. Therefore, the ejection lever 14 is mounted to the outer cylinder 12 so as to be able to pivot around the rotational shaft 17. As shown in FIG. 15, the outer cylinder 12 has the through hole 12b which penetrates through the side wall of the outer cylinder 12, and the inner cylinder 13 has the first elongated hole 13e which penetrates through the side wall of the inner cylinder 13 and extends along a longitudinal direction of the inner cylinder 13. The hook 14a of the ejection lever 14 passes through the through hole 12b of the outer cylinder 12 and the first elongated hole 13e of the inner cylinder 13 to engage with the groove 19d of the piston rod 19.

Figure 16:
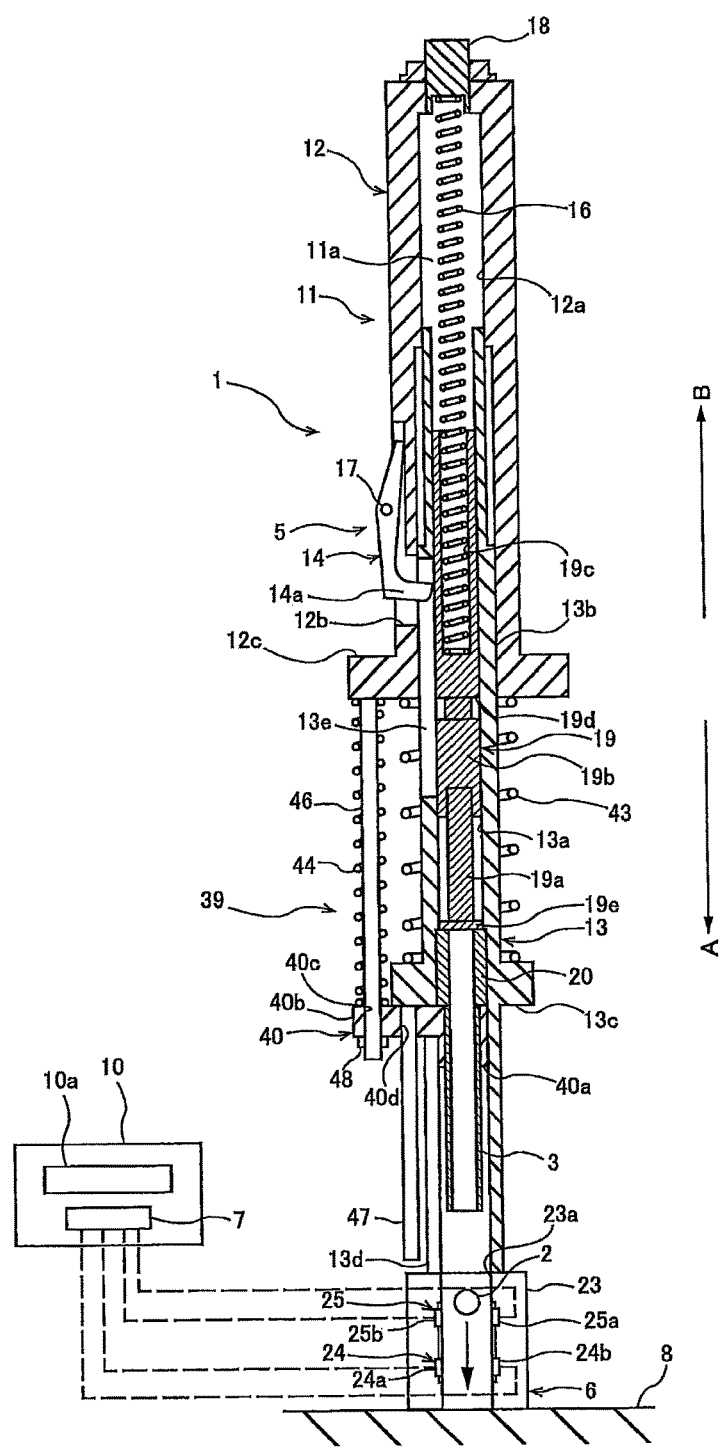
FIG. 16 is a schematic cross-sectional view showing a state in which a piston rod is pushed out in the forward direction with use of the spring force of the biasing spring when the hook of the ejection lever disengages from a groove of the piston rod.

FIG. 16 is a schematic cross-sectional view showing a state in which the piston rod 19 is pushed out in the forward direction of the ejection mechanism 5 with use of the spring force of the biasing spring 16 when the hook 14a of the ejection lever 14 disengages from the groove 19d of the piston rod 19. As shown in FIG. 16, the piston rod 19 that has been pushed out in the forward direction of the ejection mechanism 5, collides with the stopper 20, which has a hollow cylindrical shape and is fixed to the inner circumferential surface of the inner cylinder 13, and as a result, the forward movement of the piston rod 19 is restricted. During the piston rod 15 moves from the ejection position shown in FIG. 15 to a collision position shown in FIG. 16 where it collides with the stopper 20, the piston head 19e compresses air that is present in a space extending from the piston head 19e to the indenter 2. The pressure of the compressed air acts on the indenter 2 held in the front end of the holder 3, and the indenter 2 is ejected toward the specimen 8 by this pressure of the compressed air. Since movement of the piston head 19e is restricted by the stopper 20, the piston head 19e does not contact the indenter 2. In this manner, the indenter 2 may be ejected toward the specimen 8 by the air pressure acting on the indenter 2.

As described above, the length of the biasing spring 16 can be adjusted by moving the plug 18 supporting the back end of the biasing spring 16 forwards or backwards relative to the outer cylinder 12. Therefore, since the biasing force applied from the biasing spring 16 to the piston rod 19 can be adjusted, the impact speed of the indenter 2 ejected by the air which is compressed by the piston rod 19 can be adjusted. When coefficients of restitution of different specimens are to be compared, it is preferred that the material of the indenter 2 and the impact speed of the indenter 2 are constant. The apparatus 1 for measuring coefficient of restitution according to the present embodiment can easily adjust the impact speed of the indenter 2.

An experiment was carried out to confirm that the mass effect had no effect on a coefficient of restitution measured using the apparatus 1 for measuring coefficient of restitution shown in FIG. 1. Specimens used in the experiment were standard blocks, having a cylindrical shape, for the Shore hardness test, and three standard blocks whose nominal hardnesses were Shore hardness 90, Shore hardness 60, and Shore hardness 30 respectively, were used. Coefficients of restitution were measured in a case where these standard blocks were secured to a steel anvil having a mass of 5.7 kg, and coefficients of restitution were measured in a case where these standard blocks were secured to a wood anvil having a mass of 0.12 kg. FIG. 17 is a plan view of the standard block used in the experiment, and coefficients of restitution were measured at five measurement points Pa, Pb, Pc, Pd, and Pe shown in FIG. 17. The measurement point Pc is positioned at the center of the standard block, and the measurement points Pa, Pe are positioned at outer circumferential areas of the standard block. The measurement point Pb is positioned between the measurement point Pa and the measurement point Pc, and the measurement point Pd is positioned between the measurement point Pc and the measurement point Pe. As comparative examples, the D-type Shore hardness test and the Leeb hardness test were carried out on the same measurement points Pa, Pb, Pc, Pd, and Pe.

The indenter 2 used in the experiment is a bearing ball made of alumina and having a diameter of 2 mm. The mass of the indenter 2 was 0.055 g. The indenter 2 was ejected vertically downwardly. The length of the biasing spring 16 was adjusted so that the impact speed of the indenter 2 measured using the first optical sensor 24 and the second optical sensor 25 would be 10 m/s. The length of the biasing spring 16 can be adjusted by moving the plug 18 forwards or backwards relative to the outer cylinder 12.

Figure 18A:
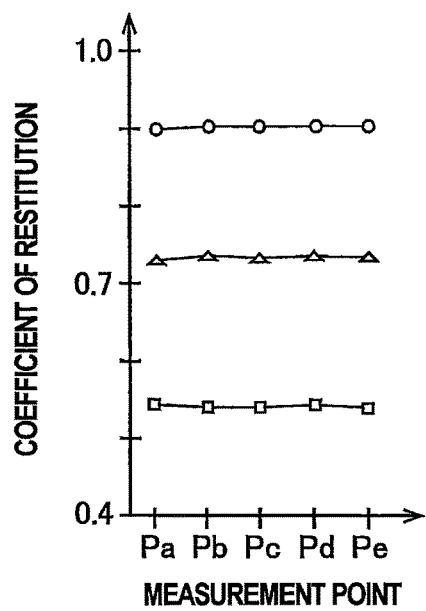
FIG. 18A is a graph indicating coefficients of restitution in a case where standard blocks fixed to the steel anvil were tested by the apparatus for measuring coefficient of restitution.
Figure 18B:
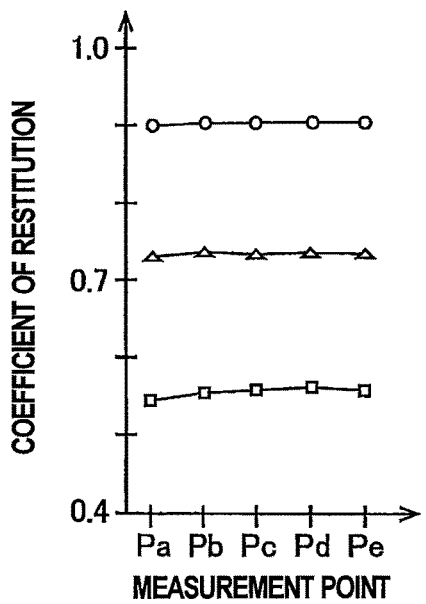
FIG. 18B is a graph indicating coefficients of restitution in a case where standard blocks fixed to the wood anvil were tested by the apparatus for measuring coefficient of restitution.

FIG. 18A is a graph indicating coefficients of restitution in the case where the standard blocks fixed to the steel anvil were tested by the apparatus 1 for measuring coefficient of restitution, and FIG. 18B is a graph indicating coefficients of restitution in the case where the standard blocks fixed to the wood anvil were tested by the apparatus 1 for measuring coefficient of restitution. As shown in FIGS. 18A and 18B, it was confirmed that there were no differences in the coefficients of restitution measured by the apparatus 1 for measuring coefficient of restitution between the case where the standard blocks were fixed to the steel anvil and the case where the standard blocks were fixed to the wood anvil, and that the coefficients of restitution were not affected by the mass effect. It was also confirmed that the same coefficients of restitution were measured at all of the five measurement points Pa, Pb, Pc, Pd, and Pe.

Figure 19A:
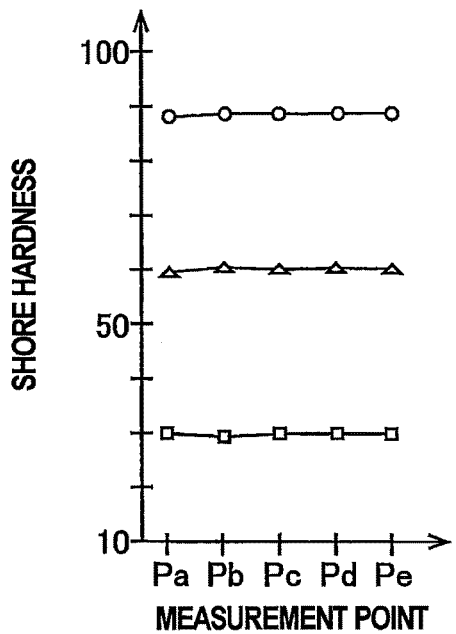
FIG. 19A is a graph indicating Shore hardnesses in a case where standard blocks fixed to the steel anvil were tested by the D-type Shore hardness tester.
Figure 19B:
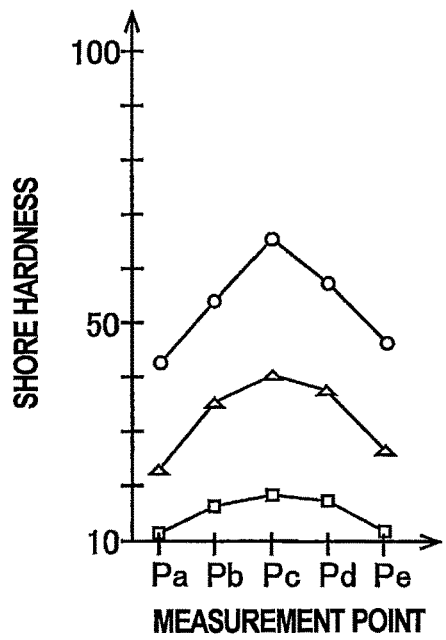
FIG. 19B is a graph indicating Shore hardnesses in a case where standard blocks fixed to the wood anvil were tested by the D-type Shore hardness tester.

FIG. 19A is a graph indicating Shore hardnesses in the case where the standard blocks fixed to the steel anvil were tested by the D-type Shore hardness tester, and FIG. 19B is a graph indicating Shore hardnesses in the case where the standard blocks fixed to the wood anvil were tested by the D-type Shore hardness tester. In the D-type Shore hardness test, a hammer including an indenter made of diamond and an indenter support member to which the indenter is secured at its front end, drops from a predetermined drop height onto the standard block, and a rebound height reached by the hammer when it has been rebounded, is measured. The Shore hardness is obtained by multiplying the ratio of the rebound height to the drop height by a predetermined proportionality constant. The mass of the hammer used in the D-type Shore hardness test was 36.2 g (including the mass of the indenter) and the drop height was 19 mm.

As shown in FIG. 19A, in the case where the standard blocks were fixed to the steel anvil, the same shore hardnesses as the nominal Shore hardnesses of the standard blocks were measured. In contrast, as shown in FIG. 19B, in the case where the standard blocks were fixed to the wood anvil, the measured Shore hardnesses were clearly smaller than the nominal Shore hardnesses, and thus it was confirmed that the mass effect due to the hammer had an effect on the measured Shore hardnesses. Furthermore, a phenomenon that the measured Shore hardnesses were gradually smaller from the central measurement point toward the measurement points in the peripheral areas was confirmed.

Figure 20A:
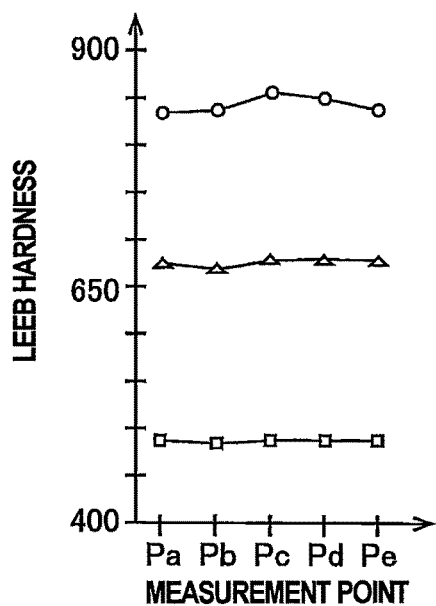
FIG. 20A is a graph indicating Leeb hardnesses in a case where standard blocks fixed to the steel anvil were tested by the Leeb hardness tester.
Figure 20B:
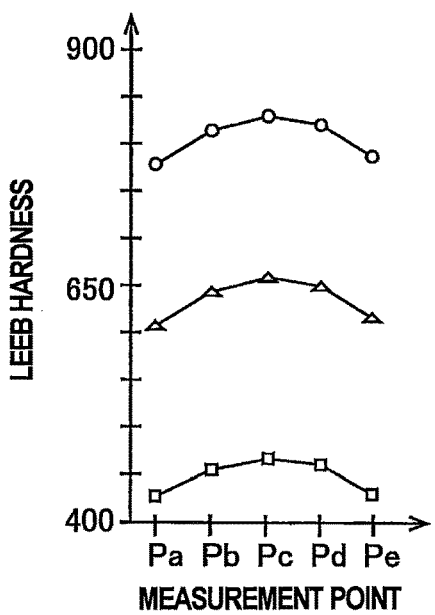
FIG. 20B is a graph indicating Leeb hardnesses in a case where standard blocks fixed to the wood anvil were tested by the Leeb hardness tester.

FIG. 20A is a graph indicating Leeb hardnesses in the case where the standard blocks fixed to the steel anvil were tested by the Leeb hardness tester, and FIG. 20B is a graph indicating Leeb hardnesses in the case where the standard blocks fixed to the wood anvil were tested by the Leeb hardness tester. The Leeb hardness test is a hardness testing method in which an impact body including an indenter and an indenter support member to which the indenter is secured at its front end, is ejected toward a specimen by a spring, and an impact speed of the impact body before impacting against the specimen and a rebound speed of the impact body when impacting against the specimen and rebounded therefrom are measured. In the Leeb hardness test, the rebound speed of the impact body with respect to the impact speed of the impact body before impacting against the specimen is measured as a coefficient of restitution. The Leeb hardness is obtained by multiplying the coefficient of restitution by a predetermined proportionality constant. The mass of the impact body used in the Leeb hardness test was 5.45 g (including the mass of the indenter), and the impact speed before the impact body impact against the specimen was 2.1 m/s.

As shown in FIGS. 20A and 20B, the Leeb hardnesses of the standard blocks fixed to the wood anvil were smaller than the Leeb hardnesses of the standard blocks fixed to the steel anvil. Therefore, it was confirmed that even in the Leeb hardness test, the mass effect due to the impact body had an effect on the measured hardnesses. Furthermore, a phenomenon that the measured Leeb hardnesses were gradually smaller from the central measurement point toward the measurement points in the peripheral areas was confirmed.

Figure 21A:
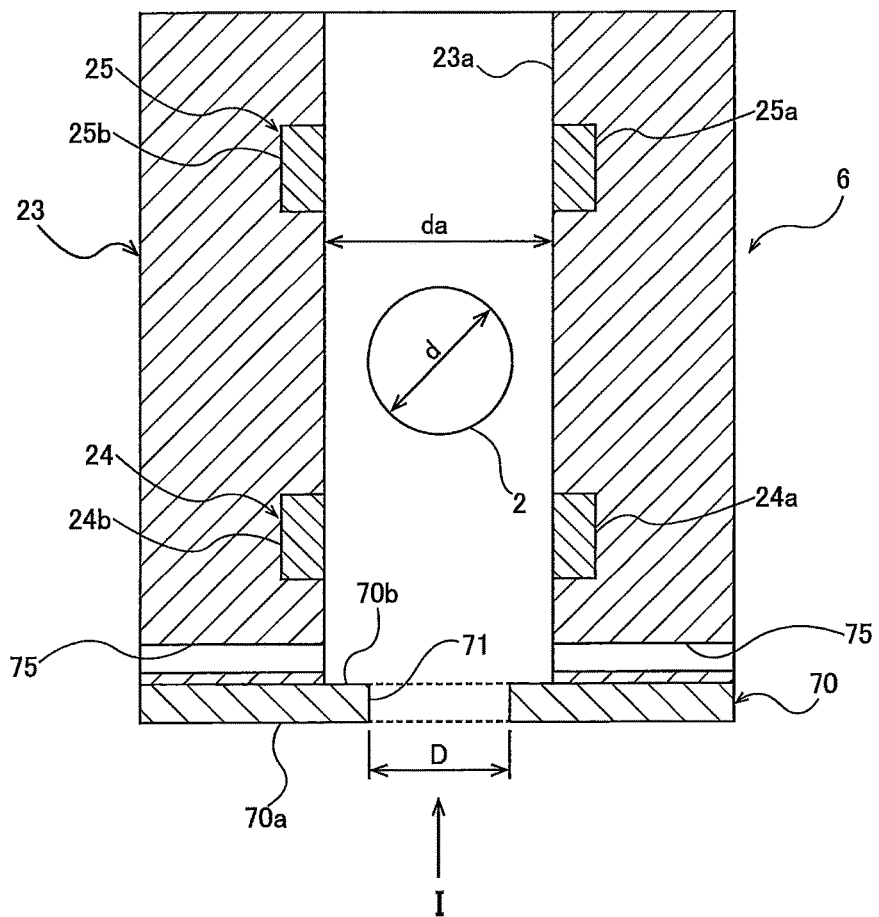
FIG. 21A is a cross-sectional view showing an example of a lid fixed to a front end of the speed measuring body.
Figure 21B:
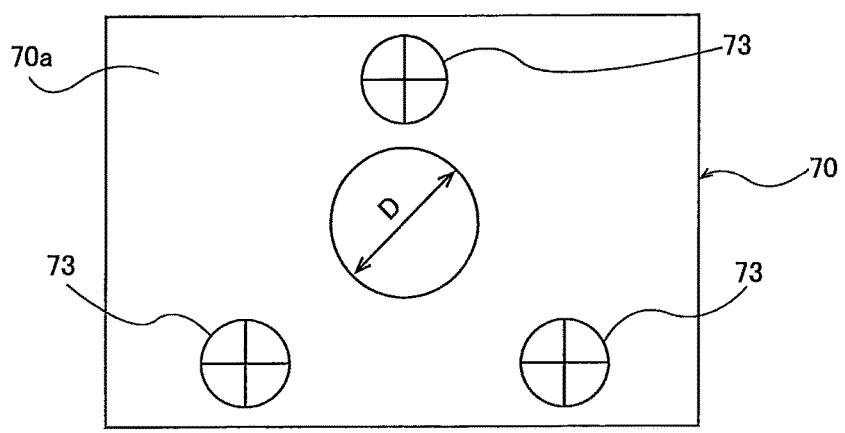
FIG. 21B is a view as viewed along arrow I in FIG. 21A.

Instead of the shutter mechanism 50 described with reference to FIGS. 7 through 11, a lid may be fixed to the front end of the speed measuring body 23 of the speed measuring unit 6, and the lid may have a lid through hole which is connected to the indenter channel 23a formed in the speed measuring body 23. FIG. 21A is a cross-sectional view showing an example of the lid 70 fixed to the front end of the speed measuring body 23, and FIG. 21B is a view as viewed along arrow I in FIG. 21A. Structures of the present embodiment other than the lid 70 are identical to those of the embodiments described above, and their repetitive descriptions are omitted.

As shown in FIG. 21A, the lid 70 fixed to the front end of the speed measuring body 23 has a lid through hole 71 which is connected to the indenter channel 23a of the speed measuring body 23. The lid through hole 71 has a hollow cylindrical shape extending from a front face 70a to a rear face 70b of the lid 70. In other words, the diameter D of the lid through hole 71 is constant from the front face 70a to the rear face 70b. A central axis of the lid through hole 71 is in alignment with the central axis of the indenter channel 23a. Further, the lid through hole 71 has a diameter D smaller than the diameter d of the indenter 2 (i.e., D<d). Therefore, the lid 70 prevents the indenter 2 from being expelled out of the apparatus 1 for measuring coefficient of restitution, because the indenter 2 cannot pass fully through the lid through hole 71.

Figure 22:
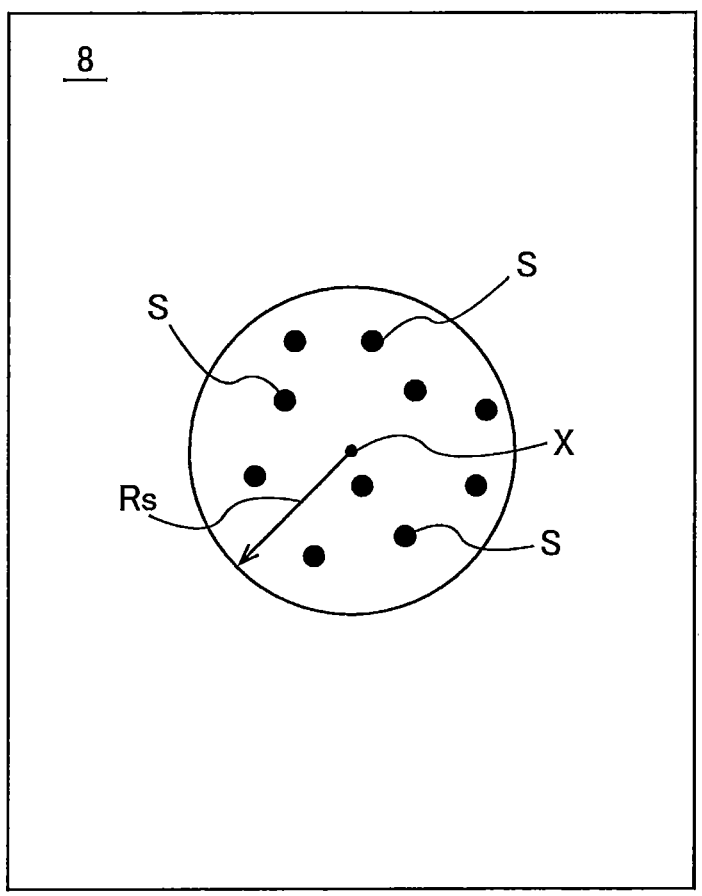
FIG. 22 is a schematic view showing an example of a distribution of impact points S where the indenter impacts against a surface of a specimen.

When the indenter 2 is ejected from the ejection mechanism 5 in a state in which the front face 70a of the lid 70 is being placed in contact with the surface of the specimen 8, the impact point where the indenter 2 impacts against the surface of the specimen 8 may deviate slightly from the point of intersection of the surface of the specimen 8 with the central axis of the lid through hole 71. FIG. 22 is a schematic view showing an example of a distribution of impact points S where the indenter 2 impacts against the surface of the specimen 8. As shown in FIG. 22, the impact points S where the indenter 2 ejected from the ejection mechanism 5 impacts against the surface of the specimen 8, lie within a circle having a radius Rs around the point X of intersection of the surface of the specimen 8 with the central axis of the lid through hole 71. It has been experimentally confirmed that the radius Rs is smaller than 0.1 times the diameter d of the indenter 2. Therefore, when the lid through hole 71 has a diameter D greater than at least 0.2 times the diameter d of the indenter 2 (i.e., 0.2 d<D), the indenter 2 ejected from the ejection mechanism 5 can impacts against the surface of the specimen 8 without colliding with the lid 70.

The lid through hole 71 has a diameter D smaller than the diameter d of the indenter 2 so that the indenter 2 is not expelled out of the apparatus 1 for measuring coefficient of restitution. On the other hand, when the indenter 2 ejected from the ejection mechanism 5 collides with the lid 70, the lid 70 may be deformed. Therefore, in order to reliably prevent the indenter 2 ejected from the ejection mechanism 5 from colliding with the lid 70, the lid through hole 71 preferably has a diameter D that is as large as possible within the range smaller than the diameter d of the indenter 2. The diameter D of the lid through hole 71 is preferably 0.5 times the diameter d of the indenter 2 or greater, and more preferably 0.7 times the diameter d of the indenter 2 or greater, or much more preferably be 0.9 times the diameter d of the indenter 2 or greater.

As shown in FIG. 21B, the lid 70 is fastened to the speed measuring body 23 by three screws (fasteners) 73. The screws 73 engage with threaded holes (not shown) formed in the speed measuring body 23, so that the lid 70 is fastened to the speed measuring body 23. The screws 73 are screwed into the threaded holes formed in the speed measuring body 23 so as not to project from the front face 70a of the lid 70. With this structure, the front face 70a of the lid 70 can directly be contacted with the surface of the specimen 8. The number of screws 73 may be less than three or more than three. Instead of the screws 73, hexagonal bolts may be used as fasteners for fastening the lid 70 to the speed measuring body 23.

The lid through hole 71 allows a part of the indenter 2 to pass through the lid 70, but the indenter 2 in its entirety cannot pass through the lid 70. The lid 70 having such lid through hole 71 is simpler in structure than the shutter mechanism 50, and thus can be manufactured less expensively than the shutter mechanism 50. As a result, a manufacturing cost of the apparatus 1 for measuring coefficient of restitution can be reduced. Further, since the diameter D of the lid through hole 71 is smaller than the diameter d of the indenter 2, the indenter 2 ejected from the ejection mechanism 5 is reliably prevented from being expelled out of the speed measuring body 23. As a result, when the indenter 2 is ejected from the ejection mechanism 5 in a state in which the front face 70a of the lid 70 is not placed in contact with the surface of the specimen 8, the indenter 2 does not collide with the operator in the vicinity of the apparatus 1 for measuring coefficient of restitution. Accordingly, the safety of operator is increased. Furthermore, a loss of the indenter 2 is effectively prevented, so that the burden on the operator is reduced.

As shown in FIG. 21A, the speed measuring body 23 may have vent holes 75 extending from side surfaces of the speed measuring body 23 to the indenter channel 23a. The vent holes 75 provided with the speed measuring body 23 prevent air in the indenter channel 23a from being compressed by the indenter 2 passing through the indenter channel 23a. If air in the indenter channel 23a is compressed by the indenter 2 ejected from the ejection mechanism 5, the impact speed of the indenter 2 may be reduced, and the rebound speed of the indenter 2 may be increased. The vent holes 75 provided with the speed measuring body 23 enables the indenter channel 23a to communicate with the exterior of the speed measuring body 23. Preferably, the vent holes 75 are provided at positions close to the front end of the speed measuring body 23. Accordingly, a more correct coefficient of restitution of the specimen 8 can be measured, because air in the indenter channel 23a is not compressed by the indenter 2 passing through the indenter channel 23a. In this embodiment, though two vent holes 75 are formed in the speed measuring body 23, the number of vent holes 75 may be one, or three or more.

A cross-sectional shape of the vent hole 75 can be determined arbitrarily. For example, the vent holes 75 may have a circular cross-sectional shape or a rectangular cross-sectional shape. The size of the vent hole 75 is preferably smaller than the size of the indenter 2. In this case, the indenter 2 is prevented from being expelled out of the speed measuring body 1 through the vent holes 75.

Figure 23:
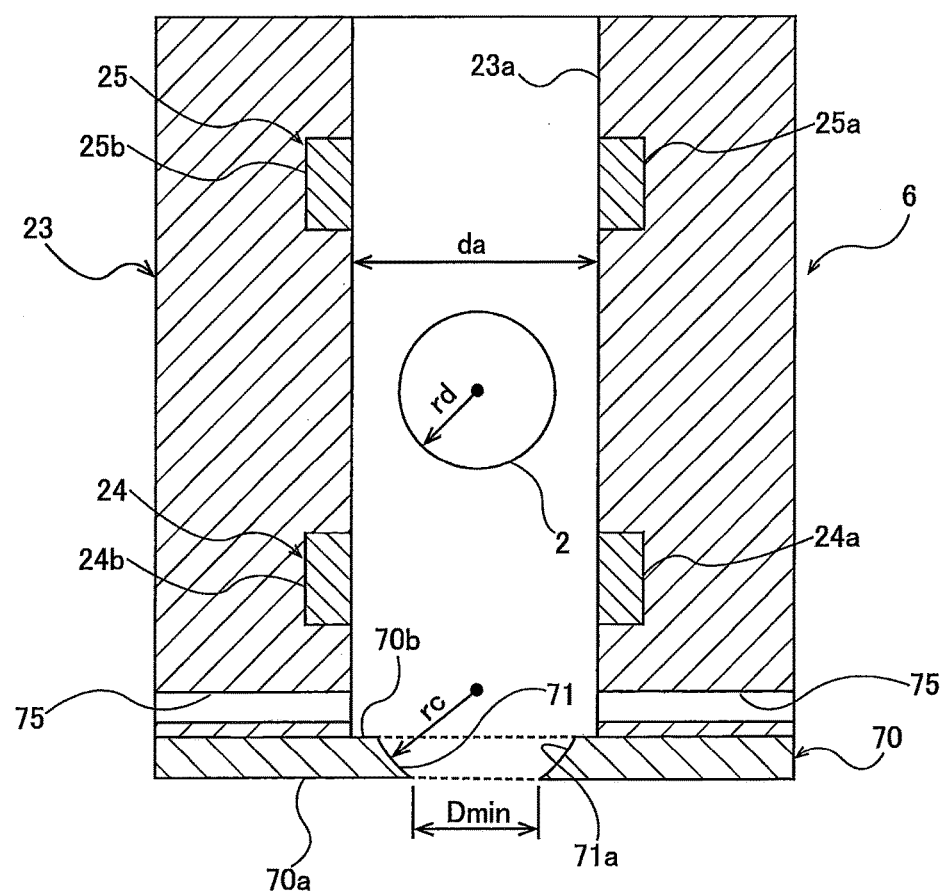
FIG. 23 is a cross-sectional view showing a modified example of the lid fixed to the front end of the speed measuring body.

FIG. 23 is a cross-sectional view showing a modified example of the lid 70 fixed to the front end of the speed measuring body 23. In the embodiment shown in FIG. 23, a wall surface 71a of the lid through hole 71 in the lid 70 is formed in a curved surface. The wall surface 71a of the lid through hole 71 has a radius rc of curvature which is constant from the front face 70a to the rear face 70b of the lid 70 and greater than the radius rd of curvature of the outer surface of the indenter 2. Since the indenter 2 has a spherical shape, the radius rd of curvature of the outer surface of the indenter 2 is the same as a radius (=d/2) of the indenter 2.

Because the wall surface 71a of the lid through hole 71 is constructed by a curved surface having the constant radius rc of curvature, the diameter D of the lid through hole 71 is gradually reduced from the rear surface 70b toward the front face 70a of the lid 70. Therefore, a minimum diameter $D_{min}$ of the lid through hole 71 is represented by a diameter of the lid through hole 71 that is open at the front face 70a of the lid 70. The minimum diameter $D_{min}$ of the lid through hole 71 is smaller than the diameter d of the indenter 2. Therefore, since the indenter 2 cannot pass fully through the lid through hole 71, the lid 70 prevents the indenter 2 from being expelled out of the apparatus 1 for measuring coefficient of restitution. Furthermore, the minimum diameter $D_{min}$ of the lid through hole 71 is at least 0.2 times the diameter d of the indenter 2. Therefore, the indenter 2 ejected from the ejection mechanism 5 can impact against the surface of the specimen 8 without colliding with the lid 70. The wall surface 71a formed in a curved surface effectively prevents the indenter 2 ejected from the ejection mechanism 5 from colliding with the lid 70.

In order to reliably prevent the indenter 2 ejected from the ejection mechanism 5 from colliding with the lid 70, the minimum diameter $D_{min}$ of the lid through hole 71 is preferably 0.5 times the diameter d of the indenter 2 or greater, and more preferably 0.7 times the diameter d of the indenter 2 or greater, or much more preferably 0.9 times the diameter d of the indenter 2 or greater.

Figure 24:
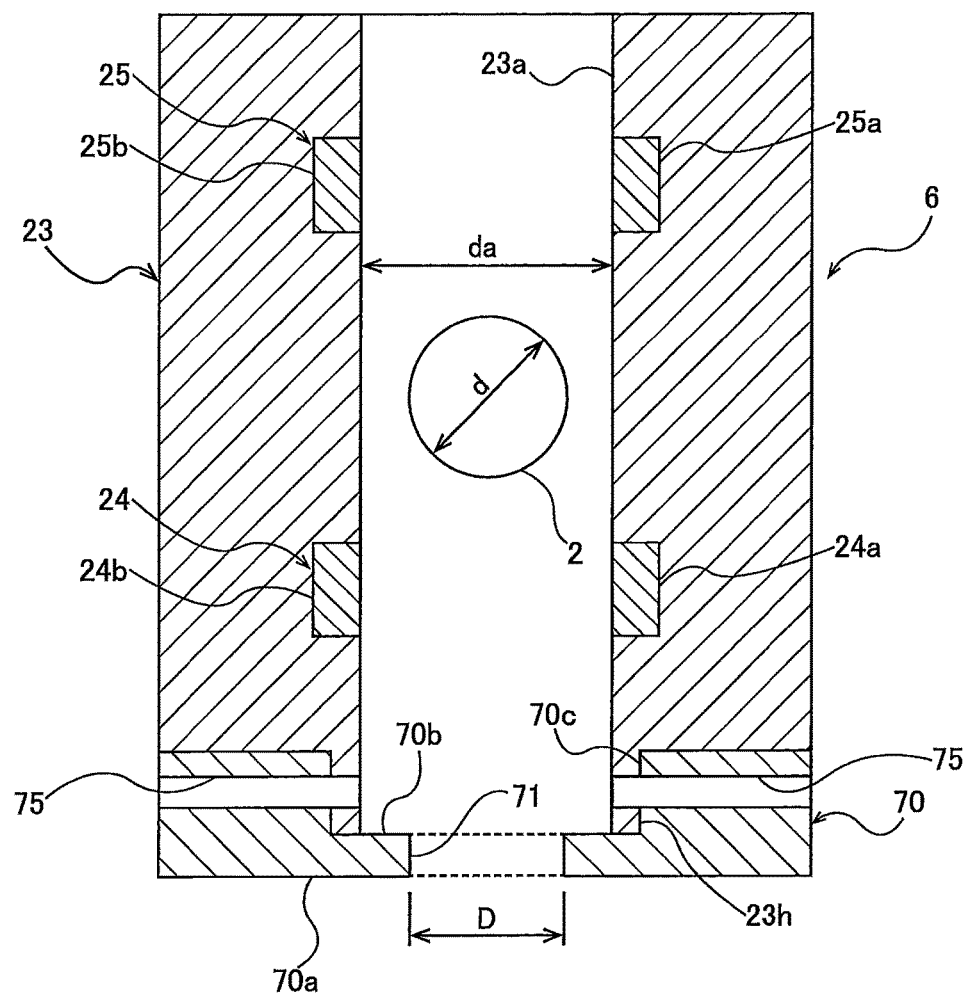
FIG. 24 is a cross-sectional view showing another modified example of the lid fixed to the front end of the speed measuring body.

FIG. 24 is a cross-sectional view showing another modified example of the lid 70 fixed to the front end of the speed measuring body 23. In the embodiment shown in FIG. 24, the front end of the speed measuring body 23 has a hollow cylindrical portion 23h, and the indenter channel 23a extends to the front end of the hollow cylindrical portion 23h. The lid 70 has a hollow cylindrical step 70c into which the hollow cylindrical portion 23h is fitted. Although the lid through hole 71 according to the present embodiment has a hollow cylindrical shape, the wall surface 71a of the lid through hole 71 may be formed in a curved surface having a constant radius rc of curvature, as shown in FIG. 23. The central axis of the lid through hole 71 can easily be aligned with the central axis of the indenter channel 23a by fitting the step 70c of the lid 70 into the hollow cylindrical portion 23h of the speed measuring body 23.

In this embodiment, the vent holes 75 extend from side surfaces of the lid 70 to the indenter channel 23a. The vent holes 75 pass through the hollow cylindrical portion 23h of the speed measuring body 23. As shown in FIG. 23, the vent holes 75 may extend from side surfaces of the lid 70 through the hollow cylindrical portion 23h to the indenter channel 23a.

Experiments were carried out to measure coefficients of restitution using the apparatus 1 for measuring coefficient of restitution in which the lid 70 shown in FIG. 21 was fixed to the front end of the speed measuring body 23. Specimens used in the experiment were standard blocks, having a cylindrical shape, for the Shore hardness test, and three standard blocks whose nominal hardnesses were Shore hardness 90, Shore hardness 60, and Shore hardness 30 respectively, were used. Using the same apparatus 1 for coefficient of restitution, coefficients of restitution of standard blocks, having a cylindrical shape, for the Rockwell hardness test were also measured. In the experiments, the ratio of the diameter da (see FIG. 21) of the indenter channel 23a to the diameter d of the indenter 2 was changed, and an effect that the relationship between the diameter da of the indenter channel 23a and the diameter d of the indenter 2 has on the measured coefficients of restitution was also evaluated. Coefficients of restitution of the same standard blocks were measured using the apparatus 1 for measuring coefficient of restitution with the shutter mechanism 50 mounted in the speed measuring body 23, and the obtained measured results were used as reference values.

The indenter 2 used in a first experiment was a bearing ball made of alumina, and the diameter d of the indenter 2 was 3 mm. The diameter D of the lid through hole 71 was 2.8 mm Therefore, the lid through hole 71 had a diameter D that was 0.93 times the diameter d of the indenter 2. The diameter da of the indenter channel 23a was 5 mm. Therefore, the indenter channel 23a had a diameter da that was 1.67 times the diameter d of the indenter 2. The length of the biasing spring 16 was adjusted so that the impact speed of the indenter 2 would be 10 m/s.

The indenter 2 used in a second experiment was a bearing ball made of alumina, and the diameter d of the indenter 2 was 3 mm. The diameter D of the lid through hole 71 was 2.8 mm. Therefore, the lid through hole 71 had a diameter D that was 0.93 times the diameter d of the indenter 2. The diameter da of the indenter channel 23a was 4 mm. Therefore, the indenter channel 23a had a diameter da that was 1.33 times the diameter d of the indenter 2. The length of the biasing spring 16 was adjusted so that the impact speed of the indenter 2 would be 10 m/s.

The indenter 2 used in a third experiment was a bearing ball made of alumina, and the diameter d of the indenter 2 was 5 mm. The diameter D of the lid through hole 71 was 4.7 mm Therefore, the lid through hole 71 had a diameter D that was 0.94 times the diameter d of the indenter 2. The diameter da of the indenter channel 23a was 7 mm. Therefore, the indenter channel 23a had a diameter da that was 1.4 times the diameter d of the indenter 2. The length of the biasing spring 16 was adjusted so that the impact speed of the indenter 2 would be 10 m/s.

In order to obtain reference values for comparing coefficients of restitution obtained in the first experiment, the second experiment, and the third experiment, coefficients of restitution of the same standard blocks were measured using the apparatus 1 for measuring coefficient of restitution with the shutter mechanism 50 mounted in the speed measuring body 23. The indenter 2 used in the experiments for obtaining the reference values was a bearing ball made of alumina, and the diameter d of the indenter 2 was 3 mm. The diameter da of the indenter channel 23a was 5 mm. Therefore, the indenter channel 23a had a diameter da that was 1.67 times the diameter d of the indenter 2. The length of the biasing spring 16 was adjusted so that the impact speed of the indenter 2 would be 10 m/s.

Coefficients of restitution obtained in the first experiment, the second experiment, and the third experiment, and coefficients of restitution measured as reference values are indicated in Table 1. The coefficients of restitution and the reference values indicated in Table 1 are average values of seven coefficients of restitution measured at different positions on the specimens.

TABLE 1

|  | Reference values | First experiment | Second experiment | Third experiment |
| --- | --- | --- | --- | --- |
| Shore hardness 95 | 0.930 | 0.930 | 0.916 | 0.936 |
| Shore hardness 80 | 0.862 | 0.868 | 0.853 | 0.870 |
| Shore hardness 30 | 0.546 | 0.547 | 0.542 | 0.546 |
| Rockwell hardness 30 | 0.626 | 0.630 | 0.619 | 0.633 |

As is clear from Table 1, the coefficients of restitution obtained in the first experiment, the second experiment, and the third experiment are essentially the same as the coefficients of restitution measured as reference values. Therefore, the apparatus 1 for measuring coefficient of restitution with the lid 70 fixed to the front end of the speed measuring body 23 can measure coefficients of restitution without being affected by the mass effect occurring in a conventional rebound hardness tester. Further, it was confirmed from the results of the first experiment and the results of the second experiment that even though the indenters 2 having different diameters d are used, the same coefficients of restitution can be obtained by fixing the impact speed of the indenter 2 to a constant.

The coefficients of restitution obtained in the second experiment are slightly smaller than the coefficients of restitution obtained in the first experiment and the coefficients of restitution obtained in the third experiment. On the other hand, the coefficients of restitution obtained in the first experiment and the coefficients of restitution obtained in the third experiment are the same as the reference values. The reason of this is considered to be the fact that the wall surface of the indenter channel 23a and the outer surface of the indenter 2 are too close to each other. Therefore, in order to obtain more correct coefficients of restitution, it is preferred that the indenter channel 23a has a diameter da which is 1.4 times the diameter d of the indenter 2 or greater. Also in the apparatus 1 for measuring coefficient of restitution with the shutter mechanism 50 mounted in the speed measuring body 23, it is preferred that the indenter channel 23a has a diameter da which is 1.4 times the diameter d of the indenter 2 or greater.

In this manner, according to the above-described apparatus 1 for measuring coefficient of restitution, the coefficient of restitution can be measured without being affected by the mass effect occurring in a conventional rebound hardness tester. Furthermore, according to the above-described apparatus 1 for measuring coefficient of restitution, there is no limitation on the direction in which the indenter 2 is ejected, because the indenter 2 is held in the holder 3. As a result, tests can be performed in free directions without being affected by the mass effect.

The apparatus 1 for measuring coefficient of restitution according to the above-described embodiments can be used as a hardness tester. Specifically, the hardness tester includes the holder 3 for holding the spherical indenter 2, the ejection mechanism 5 for ejecting the indenter 2 held by the holder 3 from this holder 3 toward the specimen 8, a speed measuring unit 6 for measuring the impact speed which represents the speed of the indenter 2 before the indenter 2 impacts against the specimen 8 and the rebound speed which represents the speed of the indenter 2 after the indenter 2 has been rebounded from the specimen 8. Further, the hardness tester includes the arithmetic unit 7, and the arithmetic unit 7 determines a hardness of the specimen 8 based on the ratio (i.e., corresponding to the coefficient of restitution) of the rebound speed of the indenter 2 to the impact speed of the indenter 2.

In the hardness tester, the indenter 2 held by the holder 3 is ejected from the holder 3 toward the specimen by the ejection mechanism 5. The speed measuring unit 6 measures the impact speed which represents the speed of the indenter 2 before the indenter 2 impacts against the specimen 8, and the rebound speed which represents the speed of the indenter 2 after the indenter 2 has been rebounded from the specimen 8. Further, the arithmetic unit 7 determines the hardness of the specimen 8 based on the ratio of the rebound speed of the indenter 2 to the impact speed of the indenter 2. For example, the arithmetic unit 7 determines the hardness of the specimen 8 by multiplying the ratio of the rebound speed of the indenter 2 to the impact speed of the indenter 2 by a predetermined proportionality constant (e.g., 100 or 1000).

If the hardness of the specimen 8 is measured by this hardness tester, the hardnesses of different specimens 8 can be compared with each other by adjusting the impact speed, which represents the speed of the indenter 2 before the indenter 2 impacts against the specimen 8, so as to be constant, and using the indenter 2 made of the same material. As described above, the impact speed of the indenter 2 can easily be adjusted by moving the plug 18 forwards or backwards relative to the outer cylinder 12.

The previous description of embodiments is provided to enable a person skilled in the art to make and use the present invention. Moreover, various modifications to these embodiments will be readily apparent to those skilled in the art, and the generic principles and specific examples defined herein may be applied to other embodiments. Therefore, the present invention is not intended to be limited to the embodiments described herein but is to be accorded the widest scope as defined by limitation of the claims and equivalents.

What is claimed is:

1. An apparatus for measuring a coefficient of restitution, comprising:
   a holder for holding a spherical indenter;
   an ejection mechanism configured to eject the indenter held by the holder from the holder to a specimen;
   a speed measuring unit configured to measure an impact speed that is a speed of the indenter before the indenter impacts against the specimen, and a rebound speed that is a speed of the indenter after the indenter is rebounded from the specimen; and
   an arithmetic unit configured to calculate a coefficient of restitution that is a ratio of the rebound speed to the impact speed,
   wherein the holder has a front end constituted by a plurality of divided portions configured to hold a circumferential surface of the spherical indenter.

2. The apparatus for measuring coefficient of restitution according to claim 1, wherein the holder has a tubular shape.

3. The apparatus for measuring coefficient of restitution according to claim 1, wherein the ejection mechanism includes:
   an inner cylinder with a through hole forming therein,
   an outer cylinder having an inner circumferential surface slidably supported by an outer circumferential surface of the inner cylinder,
   an indenter pushing member movable in the through hole, and
   a biasing spring disposed between the outer cylinder and the indenter pushing member, the biasing spring being compressed by movement of the outer cylinder to apply a biasing force to the indenter pushing member, and
   wherein the outer cylinder has an ejection lever configured to engage with a groove formed on an outer surface of the indenter pushing member.

4. The apparatus for measuring coefficient of restitution according to claim 3, wherein the indenter pushing member is a striker which collides with the indenter held by the holder.

5. The apparatus for measuring coefficient of restitution according to claim 3, wherein the indenter pushing member is a piston rod which applies an air pressure to the indenter held by the holder.

6. The apparatus for measuring coefficient of restitution according to claim 3, wherein the speed measuring unit includes
   a speed measuring body having an indenter channel which is connected to the through hole, and
   a first passage sensor and a second passage sensor which are arrayed along the indenter channel.

7. The apparatus for measuring coefficient of restitution according to claim 6, wherein the first passage sensor and the second passage sensor are optical sensors.

8. The apparatus for measuring coefficient of restitution according to claim 6, wherein the speed measuring unit further includes a third passage sensor,
   the first passage sensor, the second passage sensor, and the third passage sensor are arrayed along the indenter channel, and
   the arithmetic unit is configured to calculate an acceleration of the indenter from a speed of the indenter passing between the first passage sensor and the second passage sensor, and a speed of the indenter passing between the second passage sensor and the third passage sensor, and is further configured to calculate an impact speed at the instant at which the indenter impacts against the specimen, and a rebound speed at the instant at which the indenter is rebounded from the specimen.

9. The apparatus for measuring coefficient of restitution according to claim 8, wherein the first passage sensor, the second passage sensor, and the third passage sensor are optical sensors.

10. The apparatus for measuring coefficient of restitution according to claim 3, wherein the speed measuring unit includes
    a speed measuring body having an indenter channel which is connected to the through hole, and
    a first passage sensor and a second passage sensor which are arrayed along the indenter channel,
    wherein the first passage sensor is an optical sensor having a first light emitter and a first light receiver,
    wherein the second passage sensor is an optical sensor having a second light emitter and a second light receiver,
    wherein the first light emitter is configured to emit light through a first optical fiber into the indenter channel, and the first light receiver is configured to receive the light emitted into the indenter channel through a second optical fiber,
    wherein the second emitter is configured to emit light through a third optical fiber into the indenter channel, and the second light receiver is configured to receive the light emitted into the indenter channel through a fourth optical fiber.

11. The apparatus for measuring coefficient of restitution according to claim 3, wherein the speed measuring unit includes
    a speed measuring body having an indenter channel which is connected to the through hole, and
    a first passage sensor which is disposed in the indenter channel,
    wherein the arithmetic unit is configured to detect a detection starting point of time of the indenter at the first passage sensor and a detection ending point of time of the indenter at the first passage sensor, and
    wherein the arithmetic unit is further configured to calculate the impact speed and the rebound speed by dividing a diameter of the indenter by a time between the detection starting point of time and the detection ending point of time.

12. The apparatus for measuring coefficient of restitution according to claim 3, wherein the speed measuring unit includes a speed measuring body having an indenter channel which is connected to the through hole, and
    the speed measuring body has a shutter mechanism which opens an opening of the indenter channel when the speed measuring unit contacts the specimen, and closes the opening of the indenter channel when the speed measuring unit is separated from the specimen.

13. The apparatus for measuring coefficient of restitution according to claim 12, wherein the shutter mechanism includes
a door disposed at the opening of the indenter channel,
an opening/closing rod whose front end projects from the speed measuring body, and
a link mechanism for converting movement of the opening/closing rod into opening/closing movement of the door.

14. The apparatus for measuring coefficient of restitution according to claim 3, wherein the speed measuring unit includes:
a speed measuring body having an indenter channel connected to the through hole, and
a lid fixed to a front end of the speed measuring body, the lid having a lid through hole connected to the indenter channel,
wherein the lid through hole has a diameter which is greater than 0.2 times a diameter of the indenter, and is smaller than the diameter of the indenter.

15. The apparatus for measuring coefficient of restitution according to claim 14, wherein a wall surface of the lid through hole is formed in a curved surface, and
a radius of curvature of the wall surface is greater than a radius of curvature of the indenter.

16. The apparatus for measuring coefficient of restitution according to claim 14, wherein a vent hole extending from a side surface of the speed measuring body to the indenter channel is formed in the speed measuring body.

17. The apparatus for measuring coefficient of restitution according to claim 14, wherein the indenter channel has a diameter which is 1.4 times the diameter d of the indenter.

18. The apparatus for measuring coefficient of restitution according to claim 3, wherein the speed measuring unit includes a speed measuring body having an indenter channel which is connected to the through hole,
the apparatus further comprising a coupling mechanism for coupling the holder to the outer cylinder,
wherein the outer cylinder, the holder, the indenter, and the speed measuring unit are configured such that, when the outer cylinder moves toward the speed measuring unit, the holder moves in the forward direction in the indenter channel to hold the indenter which exists in the indenter channel.

19. The apparatus for measuring coefficient of restitution according to claim 1, wherein the indenter is made of ceramics.

20. The apparatus for measuring coefficient of restitution according to claim 19, wherein the indenter is a bearing ball made of alumina.

21. The apparatus for measuring coefficient of restitution according to claim 1, wherein a diameter of the indenter is in a range from 0.5 mm to 5 mm.

22. The apparatus for measuring coefficient of restitution according to claim 1, wherein a diameter of an inner circumferential surface of the holder is smaller than a diameter of the indenter, so that when the front end of the holder is pressed against the indenter, the divided portions are spread in an outer circumferential direction of the holder, and the circumferential surface of the indenter is held by the plurality of divided portions.

23. The apparatus for measuring coefficient of restitution according to claim 1, wherein the front end of the holder has slits extending parallel to an axis of the holder to form the plurality of divided portions.

24. The apparatus for measuring coefficient of restitution according to claim 1, wherein the arithmetic unit is configured to determine a hardness of the specimen based on the calculated coefficient of restitution.

25. A hardness tester, comprising:
a holder for holding a spherical indenter;
an ejection mechanism configured to eject the indenter held by the holder from the holder to a specimen;
a speed measuring unit configured to measure an impact speed that is a speed of the indenter before the indenter impacts against the specimen, and a rebound speed that is a speed of the indenter after the indenter is rebounded from the specimen; and
an arithmetic unit configured to decide hardness of the specimen based on a ratio of the rebound speed to the impact speed,
wherein the holder has a front end constituted by a plurality of divided portions which are configured to hold a circumferential surface of the indenter.

26. The apparatus for measuring coefficient of restitution, comprising:
a holder for holding a spherical indenter;
an ejection mechanism configured to eject the indenter held by the holder from the holder to a specimen;
a speed measuring unit configured to measure an impact speed that is a speed of the indenter before the indenter impacts against the specimen, and a rebound speed that is a speed of the indenter after the indenter is rebounded from the specimen; and
an arithmetic unit configured to calculate a coefficient of restitution that is a ration of the rebound speed to the impact speed,
wherein the ejection mechanism includes:
an inner cylinder with a through hole formed therein,
an outer cylinder having an inner circumferential surface slidably supported by an outer circumferential surface of the inner cylinder,
an indenter pushing member movable in the through hole, and
a biasing spring disposed between the outer cylinder and the indenter pushing member, the biasing spring being compressed by movement of the outer cylinder to apply a biasing force to the indenter pushing member, and
wherein the outer cylinder has an ejection lever configured to engage with a groove formed on an outer surface of the indenter pushing member.

27. A hardness tester, comprising:
a holder for holding a spherical indenter;
an ejection mechanism configured to eject the indenter held by the holder from the holder to specimen;
a speed measuring unit configured to measure an impact speed that is a speed of the indenter before the indenter impacts against the specimen, and a rebound speed that is a speed of the indenter after the indenter is rebounded from the specimen; and
an arithmetic unit configured to decide hardness of the specimen based on a ration of the rebound speed to the impact speed,
wherein the ejection mechanism includes:
an inner cylinder with a through hole formed therein,
an outer cylinder having an inner circumferential surface slidably supported by an outer circumferential surface of the inner cylinder,
an indenter pushing member movable in the through hole, and
a biasing spring disposed between the outer cylinder and the indenter pushing member, the biasing spring being compressed by movement of the outer cylinder to apply a biasing force to the indenter pushing member, and wherein the outer cylinder has an ejection lever configured to engage with a groove formed on an outer surface of the indenter pushing member.

* * * * *